US010269113B2

(12) United States Patent
Petit

(10) Patent No.: US 10,269,113 B2
(45) Date of Patent: Apr. 23, 2019

(54) METHOD OF ANALYZING FACIAL IMAGES FOR DETECTING A FLUSH EFFECT

(71) Applicant: GALDERMA RESEARCH & DEVELOPMENT, Biot (FR)

(72) Inventor: Laurent Petit, Peymeinade (FR)

(73) Assignee: GALDERMA RESEARCH & DEVELOPMENT, Boit (FR)

( * ) Notice: Subject to any disclaimer, the term of this patent is extended or adjusted under 35 U.S.C. 154(b) by 67 days.

(21) Appl. No.: 15/107,369

(22) PCT Filed: Dec. 23, 2014

(86) PCT No.: PCT/EP2014/079227
§ 371 (c)(1),
(2) Date: Nov. 28, 2016

(87) PCT Pub. No.: WO2015/097239
PCT Pub. Date: Jul. 2, 2015

(65) Prior Publication Data
US 2017/0076444 A1 Mar. 16, 2017

(30) Foreign Application Priority Data
Dec. 23, 2013 (FR) ..................................... 13 63400

(51) Int. Cl.
*A61B 5/00* (2006.01)
*G06T 7/00* (2017.01)
(Continued)

(52) U.S. Cl.
CPC .......... *G06T 7/0012* (2013.01); *A61B 5/0077* (2013.01); *A61B 5/1032* (2013.01); *A61B 5/441* (2013.01); *G06K 9/00228* (2013.01); *G06T 7/0016* (2013.01); *A61B 2576/02* (2013.01); *G06T 2207/10024* (2013.01); *G06T 2207/30088* (2013.01); *G06T 2207/30201* (2013.01)

(58) Field of Classification Search
CPC .................................... G06K 9/00; G06T 7/00
USPC .................. 382/103, 236; 348/169–172, 352
See application file for complete search history.

(56) References Cited

U.S. PATENT DOCUMENTS 7,324,669 B2 * 1/2008 Nakanishi .............. G03B 17/53
104/203
9,256,720 B2 * 2/2016 Berini ...................... G06F 21/32

FOREIGN PATENT DOCUMENTS

JP 2007152084 A 6/2007
WO 2013/122233 A1 8/2013

OTHER PUBLICATIONS

International Search Report dated Mar. 5, 2015 corresponding to International Patent Application No. PCT/EP2014/079227 with English translation, 8 pages.
(Continued)

*Primary Examiner* — Abolfazl Tabatabai
(74) *Attorney, Agent, or Firm* — Sunit Talapatra; Foley & Lardner LLP

(57) ABSTRACT

A method is described for analyzing images of the face of a human being. The method can include the following steps:
—acquiring at least one image of the face such that the nose, the eyes and the cheeks are aligned on pre-existing markers,
—determining the components of the image in at least one zone of the face, —comparing the components to stored values, and —determining the presence of a flush effect if the components are greater than the stored values.

10 Claims, 43 Drawing Sheets

(51) Int. Cl.
  *A61B 5/103*    (2006.01)
  *G06K 9/00*     (2006.01)

(56) References Cited

OTHER PUBLICATIONS

Wagner, J.K., et al., "Comparing Quantitative Measures of Erythema, Pigmentation and Skin Response using Reflectometry," Pigment Cell Research, vol. 15, No. 5, Oct. 2002, pp. 379-384.
Takiwaki, H., et al., "Mearsurement of skin color: practical application and theoretical considerations," The Journal of Medical Investigation, vol. 44, Feb. 1998, pp. 121-126.
Fullerton, A., et al., "Guidelines for measurement of skin colour and erythema—A report from the Standardization Group of the European Society of Contact Dermatitis," vol. 35, No. 1, Jan. 1996, pp. 1-10.
Yang, X., et al., "Visage: A Face Interpretation Engine for Smartphone Applications," Jan. 2013, XP055171510, pp. 149-168.

* cited by examiner

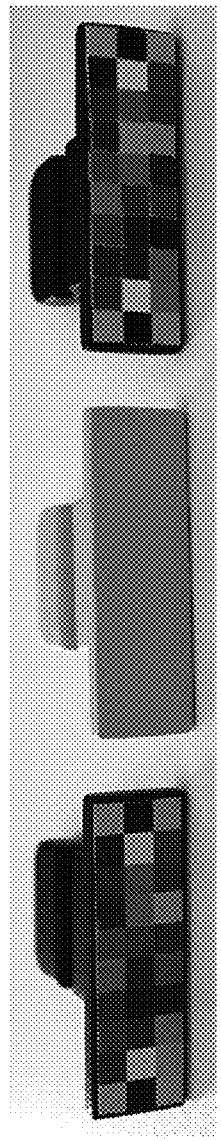

METHOD OF ANALYZING FACIAL IMAGES FOR DETECTING A FLUSH EFFECT

CROSS-REFERENCE TO PRIOR APPLICATIONS

This application is a National Stage of PCT/EP2014/079227, filed Dec. 23, 2014, and designating the United States (published on Jul. 2, 2015, as WO 2015/097239 A1), which claims priority under 35 U.S.C. § 119 to French Patent Application No. 1363400, filed Dec. 23, 2013, each hereby expressly incorporated by reference in its entirety and each assigned to the assignee hereof.

The technical field of the invention is skin analysis, and more particularly the analysis of the trend of the colorimetric parameters of the skin.

The subject of the invention is a method for analyzing images of the face of a human being comprising the following steps:
- at least one image of the face is acquired such that the nose, the eyes and the cheeks are aligned on pre-existing markers,
- the components of the image are determined in at least one zone of the face,
- the components are compared to stored values, and
- the presence of a flush effect is determined if the components are greater than the stored values.

The zones of the face can be the cheeks.

The components can be the colorimetric components L* (lightness), a* (red/green axis), b* (yellow/blue axis).

The stored values can be the values of the colorimetric components determined at an earlier date for the same face.

The presence of a flush effect can be determined if the colorimetric component associated with the color red is greater than the stored value associated with the color red.

The acquisition of images can be performed using a smartphone or PDA phone.

Moreover, the vertical alignment of the acquisition of images can be ensured by an internal sensor of a smartphone, for example a triaxial gyroscope.

The acquisition can be performed while the subject holds a colorimetric color chart via the mouth, in order to correct the colorimetric components.

At least one parameter can be acquired that is chosen from the temperature, the atmospheric pressure, the ambient brightness and the relative humidity, in order to correct the colorimetric components of any environmental effect on the face.

Advantageously, the values of the colorimetric components determined can be configured for a self-assessment of skin disorders such as melasma, nevus, rosacea, erythema, reddening, acne, psoriasis, dermatitis, actinic keratosis, rash and seborrheic dermatitis.

Other aims, features and advantages of the invention will become apparent on reading the following description, given purely as a nonlimiting example and with reference to the attached drawings.

BRIEF DESCRIPTION OF THE DRAWINGS

FIGS. 4a, 4b and 4c illustrate colorimetric color charts.

A technical protocol will be described first that makes it possible to analyze the flush effect or abrupt reddening on a face. The aim is to quantify the alteration of color of the face, which becomes more red, during this flush effect, the aim being to conduct a clinical study to demonstrate the reduction of these effects with the taking of a specific active principle. Advantageously, this study can be used for a self-assessment of skin disorders such as melasma, nevus, rosacea, erythema, reddening, acne, psoriasis, dermatitis, actinic keratosis, rash and seborrheic dermatitis.

A first study made it possible to define a most optimal portable system for the acquisition of photos in portrait mode. It was decided to use two distinct camera systems, namely a first and a second device respectively marketed by the company Samsung under the brands:

Samsung Galaxy S4®

Samsung Galaxy S4 Mini®

The aim is to characterize the two chosen acquisition systems and to validate the acquisition sensitivity as a function of the conditions of illumination and of the shooting environment.

After a description of the specifications of the two systems and of the acquisition software hereinafter referred to by the term "SmartCam" developed specifically for this application, the acquisition protocol and the analysis methods will be detailed.

The results, the problems encountered and the solutions and recommendations considered will then be detailed.

A practical use of the software application embedded in the camera systems will finally be described with reference to FIGS. 41a, 41b, 42a, 42b and 43 in the context of a treatment of a flush with Brimonidine.

To perform all the acquisitions, as indicated previously, two smartphones are used, namely the telephone marketed under the brand name Samsung Galaxy S4, and a Samsung Galaxy S4 Mini telephone which has a smaller bulk but performs levels a little lower than the Samsung Galaxy S4. With the second telephone, S4 Mini, the resolution of the camera is slightly lower and not all of the humidity, temperature and relative humidity sensors are present.

The characteristics of the first device (Samsung Galaxy S4) are as follows:

| | |
|---|---|
| Dimensions | 136.6 × 69.8 × 7.9 mm |
| Weight | 130 g |
| Front camera resolution | 2.1M pixels (1920 × 1080) |
| Back camera resolution | 13M pixels |
| Operating system | Android |
| Telephone | Yes |
| GPS | Yes |
| Sensors | Proximity, light, ambient, thermometer, hygrometer, barometer, accelerometer, triaxial gyroscope, magnetometer |

The characteristics of the second device (Samsung® Galaxy S4 Mini) are as follows:

| | |
|---|---|
| Dimensions | 124.6 × 61.3 × 8.9 mm |
| Weight | 107 g |
| Front camera resolution | 1.9M pixels (1392 × 1392) |
| Back camera resolution | 8M pixels |
| Operating system | Android |
| Telephone | Yes |
| GPS | Yes |
| Sensors | Proximity, accelerometer, triaxial gyroscope, magnetometer |

Figure 1B:
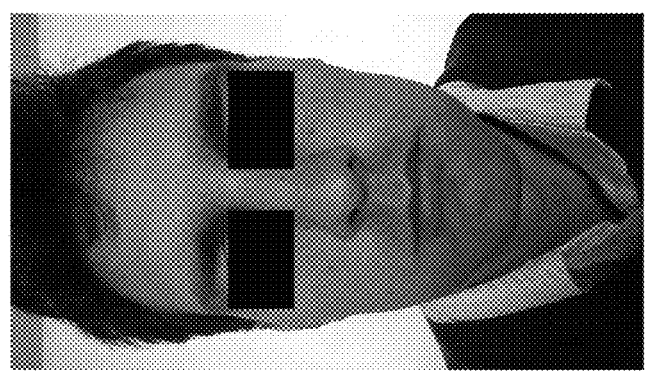
FIGS. 1a and 1b illustrate examples of photographs acquired with two different acquisition systems.
Figure 1A:
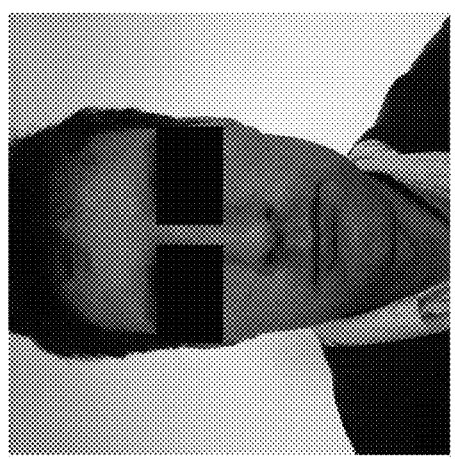

In order to compare the two systems, a series of photos were taken in the same lighting conditions and at a few second intervals with the Samsung Galaxy S4 and the Samsung Galaxy S4 Mini. FIGS. 1a and 1b show examples of photos acquired with the two systems, FIG. 1a being acquired with the Samsung Galaxy S4 Mini (1393×1393) and FIG. 1b being acquired with the Samsung Galaxy S4 (1080×1920).

It is then observed that the resolution of the Galaxy S4 Mini is square (1393×1393 pixels) and a subject needs to be positioned a little further away from the lens compared to the Galaxy S4 (1080×1920 pixels).

The positioning further away from the lens results in a reduction of the optical distortions (commonly referred to by those skilled in the art as "fish-eye effects") which are slightly visible with the Samsung® Galaxy S4. Since the analysis of the photos is focused on non-morphological analyses, that has no negative effects. By contrast, it is noted that, in the same acquisition environment, the Galaxy S4 takes brighter photos and the gloss also is more clearly visible on the skin. The images are also more contrasted with the Galaxy S4 compared with the Samsung Galaxy S4 Mini.

And the details are also more visible with the Galaxy S4 than on the Galaxy S4 Mini.

Moreover, data acquisition software, embedded in the telephones, notably makes it possible:
  to define, at the start of the study, two horizontal axes on the photo in "live" mode (real time) making it possible to align the eyes and the mouth of the subject,
  to allow the rapid repositioning of the subject using these two horizontal axes and a vertical axis,
  to define a vertical tilt indicator making it possible to limit the variability of image acquisition angle,
  to store the images acquired in high definition (maximum resolution of the device) in JPEG format, and
  to store the data relating to each image capture such as the date and time but also the information from the different sensors: ambient brightness, atmospheric pressure, temperature, humidity and vertical tilt.

Figures 2A, 2B, 2C:
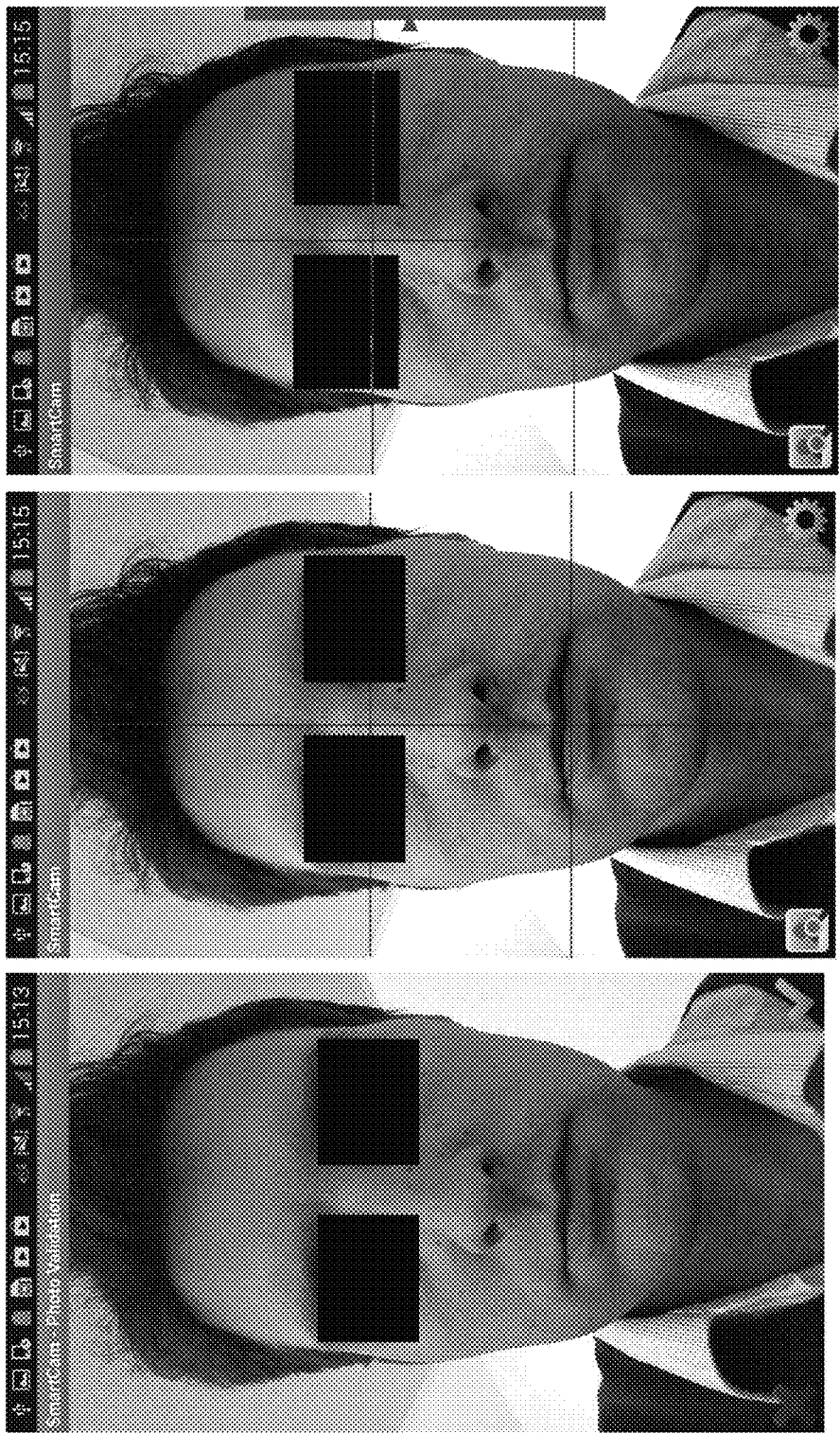
FIGS. 2a, 2b, 2c, 3a and 3b illustrate the operation of acquisition software.

When the software is launched, the "live" mode is displayed directly with the horizontal axes and the vertical axis (FIG. 2a). These axes were defined in the administration zone of the software at the start of the study.

The user is positioned in front of the camera and best adjusts his or her face to align it on the markers.

Once the subject is well positioned, he or she presses on the screen to take the photo. A new window appears with the photo acquired in full resolution and the user can choose to retain it or cancel it (FIG. 2b).

The software application also makes it possible to display a tilt indicator on the interface (center right) of the software in "live" mode to force the correct positioning of the device vertically (green zone of the tilt indicator) at the image capture time (FIG. 2c).

When the photo is validated, the latter is stored in the "Pictures//SmartCam" folder of the device and the related data are stored in the database.

Figure 3B:
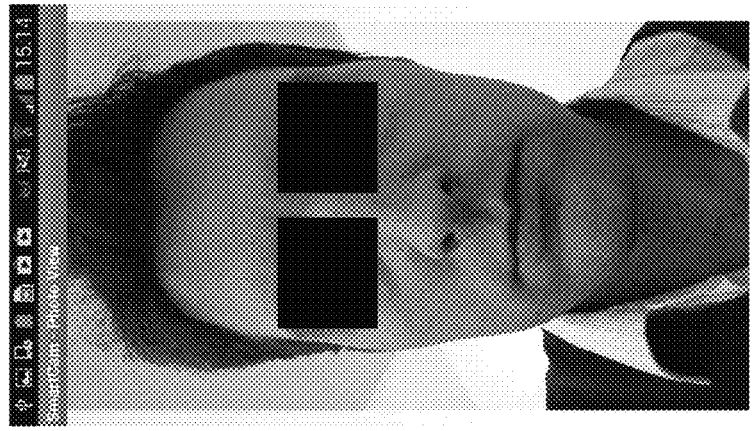
Figure 3A:
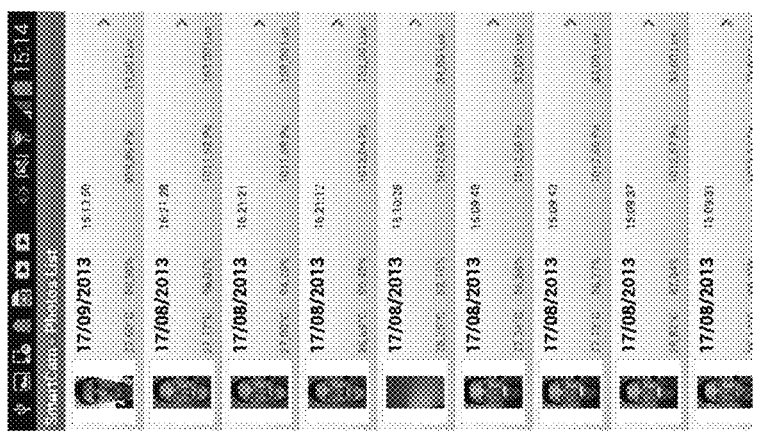

All of these data can be consulted by the user (FIG. 3a). The list of all the photos acquired is then retrieved with the date, time, ambient brightness and, on the devices that permit it: the temperature, the relative humidity and the atmospheric pressure.

The user can also see the photos in full screen with a dedicated interface (FIG. 3b) with the possibility of zooming in on the photo to see the details.

In the administration part of the software, it is possible to export all the data stored in the database to generate a text file formatted to be easily imported into Microsoft Excel®.

In order to quantify the lighting drifts and correct them as a function of the different acquisition environments, three specific color charts (FIGS. 4a, 4b and 4c) are used to implement a feasibility study:
  a numeric color chart of 30 patches of color in 40×12 mm format with 4×4 mm patches (FIG. 4a),
  a uniform gray color chart (FIG. 4b), and
  a color chart with 30 diffuse Munsell patches in 40×12 mm format with 4×4 mm patches (FIG. 4c).

Figure 5B:
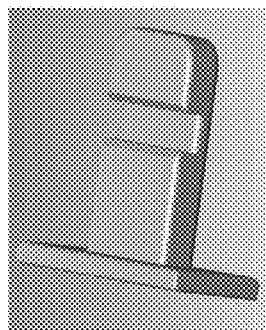
FIGS. 5a and 5b illustrate two views of a colorimetric color chart support.
Figure 5A:
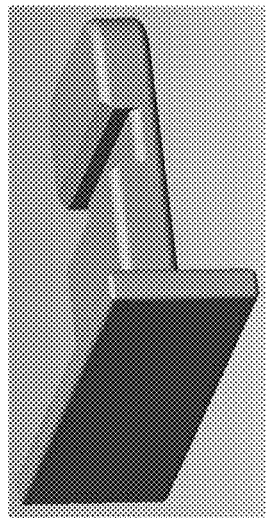

A specific support in CAD (FIGS. 5a and 5b) is also used to make it possible for the user to position the color chart in front of his or her mouth reproducibly.

The data acquisition protocol must primarily make it possible:
  to validate the commissioning of the "SmartCam" acquisition software, to validate the quality (resolution, colorimetric rendition) of the resulting images, to study the performance levels of the different colorimetric color charts, and to analyze the acquisition variabilities as a function of the environment.

The acquisition system must be placed as vertically as possible in front of the face.

The face must cover all of the field of acquisition to maintain the correct resolution.

During the first image capture, the user must define the repositioning guides by moving the red and green cursors over the eyes and the mouth.

He or she must not modify the repositioning guides during the study.

It is nevertheless possible to move the axes (parameter menu bottom right) right at the very start of the study if they are not correctly positioned.

An image capture is performed according to the following procedure:

position the color chart in your mouth by holding it by the groove with the teeth on the home screen of the "SmartCam" acquisition software display: "position yourself as best possible to be centered relative to the vertical axis and relative to the horizontal guides for the mouth and the eyes", click anywhere in the image to take the photo a window will appear with the acquired photo, validate it if it is correct (no blurring, correct positioning) or cancel to recommence.

The photos acquired cannot be deleted from the "SmartCam" software.

The photos acquired can be consulted by clicking on the button on the bottom left of the home screen. The list of all the acquisitions appears and it is possible to click on an element to see the photo in full resolution on the screen.

It is necessary to correctly check that the color chart is present in each photo (otherwise it will not be usable).

It would be at least necessary to perform the steps at least for 10 consecutive days. The subsequent image captures must be done in normal conditions (no particular prior effort) and if possible at fixed times and in the same environment:

3 consecutive acquisitions with the color chart in the morning (get up)

3 consecutive acquisitions at midday with the midday color chart (if possible in the same environment as in the morning)

3 consecutive acquisitions in the evening with the evening color chart (at bedtime).

Other image captures can be performed:

during the day and in different places outside and inside always with the color chart and always 3 times consecutively to analyze the reproducibility of the system, and in particular conditions (after sport, after a period of exposure to the sun, etc.)

Following all the acquisitions performed, the following photos are available:

51 photos of a first individual taken with a Galaxy S4 Mini distributed as follows:

17 photos with 3 repeats, i.e. 51 photos with the numeric color chart;

168 photos of a second individual with a Galaxy S4 distributed as follows:

28 photos with 3 repeats, i.e. 84 photos with the numeric color chart, and 28 photos with 3 repeats, i.e. 84 photos with the gray color chart;

450 photos taken with a Galaxy S4 distributed as follows:

50 photos with 3 repeats, i.e. 150 photos with the numeric color chart, 50 photos with 3 repeats, i.e. 150 photos with the gray color chart, and 50 photos with 3 repeats, i.e. 150 photos with the Munsell color chart.

In other words, a total of 669 photos to be analyzed.

In order to define which color chart is the most efficient, the relative deviations of the 3 components $L^*$, $a^*$ and $b^*$ are analyzed over a set of 50 acquisitions with 3 repeats each time. The photos were acquired with the first device, a Samsung Galaxy S4.

Each photo was readjusted colorimetrically by colorimetric readjustment algorithms with adjustment of the convergence constraints given the variations between each image capture condition which are very significant.

For the 30-patch color charts, multi-patch colorimetric readjustment algorithms were used whereas, for the gray color chart, a technique of "white point compensation" type was used.

The colorimetric readjustment results are compared with each color chart on the components $L^*$, $a^*$ and $b^*$ for a defined zone on each cheek. The standard deviation of the mean values of the 2 cheeks (table 1) is computed over the 3 repeats after colorimetric readjustment.

TABLE 1

Mean relative standard deviation of the 2 cheeks with 3 repeats of 50 acquisitions for each color chart type

| | $\sigma (L^*)$ | $\sigma (a^*)$ | $\sigma (b^*)$ |
|---|---|---|---|
| 30-patch numeric color chart | 1.44 | 0.77 | 0.21 |
| Gray color chart | 1.65 | 1.20 | 1.37 |
| 30-patch Munsell color chart | 1.46 | 0.95 | 1.04 |

It is observed that the relative deviations (table 1) between 3 repeats after colorimetric correction are at the same order of magnitude whatever the color chart used. The observed variations seem less great with the 30-patch numeric color chart. In effect, this exhibits a slightly glossy film which can optimize the colorimetric correction.

The efficiency of the colorimetric correction (table 2) will be studied below over all of the 30 patches of the numeric color chart over the 150 photos acquired (50 photos with 3 repeats) with this color chart.

TABLE 2

Average variabilities of the 30 patches of the numeric color chart before and after colorimetric correction over 150 photos

| | $\sigma (L^*)$ | $\sigma (a^*)$ | $\sigma (b^*)$ |
|---|---|---|---|
| Before readjustment | 6.62 | 6.75 | 9.32 |
| After readjustment | 2.64 | 3.61 | 5.14 |

A significant decrease is observed on all of the colorimetric parameters $L^*$, $a^*$ and $b^*$.

The average colorimetric variability over all hues is optimized by close to 50%. All the photos analyzed in the rest of this study will be those which are readjusted relative to the 30-patch numeric color chart.

The reproducibility of the acquisition with the colorimetric readjustment will now be described. Ten successive image captures are carried out with a numeric colorimetric color chart. Each acquisition is performed in the same environment but the color chart is removed then repositioned between each acquisition.

The results presented in table 3 below therefore take account of the variability of repositioning of the color chart.

TABLE 3

Average variabilities on the colorimetric parameters of the cheeks over 10 photos taken in succession in the same environment.

|  | σ (L*) | σ (a*) | σ (b*) |
|---|---|---|---|
| Left cheek | 1.20 | 0.73 | 0.16 |
| Right cheek | 1.19 | 0.52 | 0.14 |

It is observed that the variabilities are substantially identical for the right cheek and the left cheek. The variability is greater on the lightness component L* than on the other components a* and b*.

The results show that the accuracy of the measurement will be of the order of +/− 1.5 units in L* and of the order of +/−1 unit in a* and +/− 0.5 unit in b* for the acquisitions performed in the same environment and in the same lighting conditions.

The variabilities on each colorimetric component L*, a* and b* have moreover been analyzed for all the repeats regardless of the acquisition environment for each subject (tables 4a, 4b and 4c).

TABLE 4a

Variabilities on the colorimetric parameter L* of the cheeks (right and left) over 3 repeats over all the photos acquired.

|  |  |  | σ (L*) | | |
|---|---|---|---|---|---|
|  | Acquisition | Repeat | Min | Average | Max |
| Individual 1 | 17 | 3 | 0.17 | 1.48 | 7.05 |
| Individual 2 | 28 | 3 | 0.18 | 0.95 | 3.77 |
| Individual 3 | 50 | 3 | 0.12 | 1.23 | 6.99 |

TABLE 4b

Variabilities on the colorimetric parameter a* of the cheeks (right and left) over 3 repeats over all the photos acquired.

|  |  |  | σ (a*) | | |
|---|---|---|---|---|---|
|  | Acquisition | Repeat | Min | Average | Max |
| Individual 1 | 17 | 3 | 0.09 | 1.05 | 3.77 |
| Individual 2 | 28 | 3 | 0.11 | 0.64 | 2.78 |
| Individual 3 | 50 | 3 | 0.04 | 0.97 | 3.83 |

TABLE 4c

Variabilities on the colorimetric parameter b* of the cheeks (right and left) over 3 repeats over all the photos acquired.

|  |  |  | σ (b*) | | |
|---|---|---|---|---|---|
|  | Acquisition | Repeat | Min | Average | Max |
| Individual 1 | 17 | 3 | 0.06 | 1.31 | 6.00 |
| Individual 2 | 28 | 3 | 0.30 | 0.87 | 1.80 |
| Individual 3 | 50 | 3 | 0.07 | 1.17 | 2.95 |

It is noted that the overall average variabilities are relatively good for each component. Relatively significant maximum variabilities are nevertheless observed, above all on the component L*, which are mainly due to the variations of illumination with each acquisition condition.

The colorimetric trend on the cheeks of each of the 3 subjects (individuals 1, 2 and 3) will now be analyzed over time.

Firstly, the overall time effect will be analyzed over 20 days.

This analysis was performed on the photos taken by individual 1 over 20 days with the second Galaxy S4 Mini device with a total of 51 photos.

The colorimetric data are extracted on both cheeks after colorimetric readjustment with the 30-patch numeric color chart.

Figure 6:
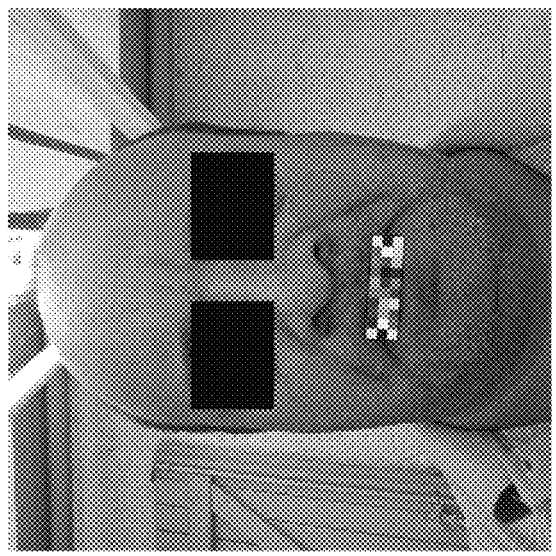
FIG. 6 illustrates the zones analyzed on a photograph, FIGS. 7, 8 and 9 respectively illustrate the trend of the colorimetric parameters L*, a* and b* as a function of time, over 20 days.

The analysis zones were defined manually on each photo as shown in FIG. 6.

Figure 7:
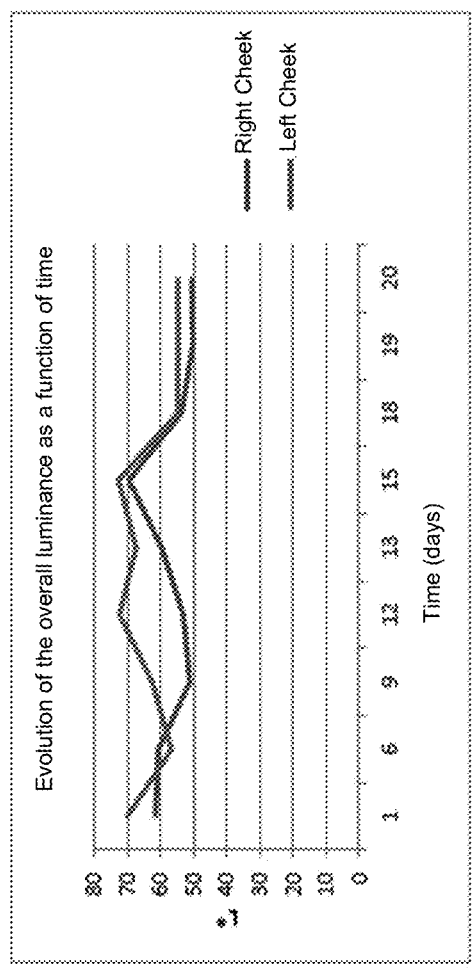
Figure 8:
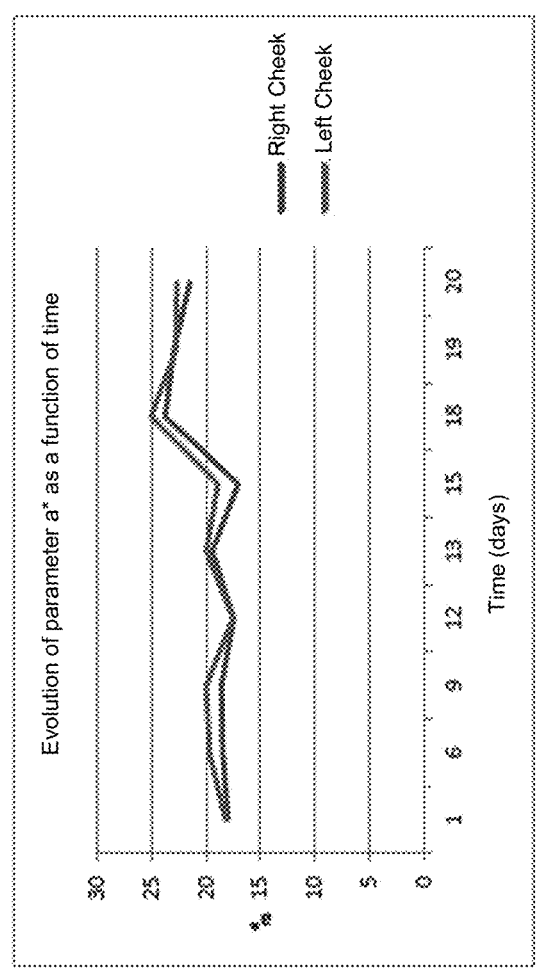
Figure 9:
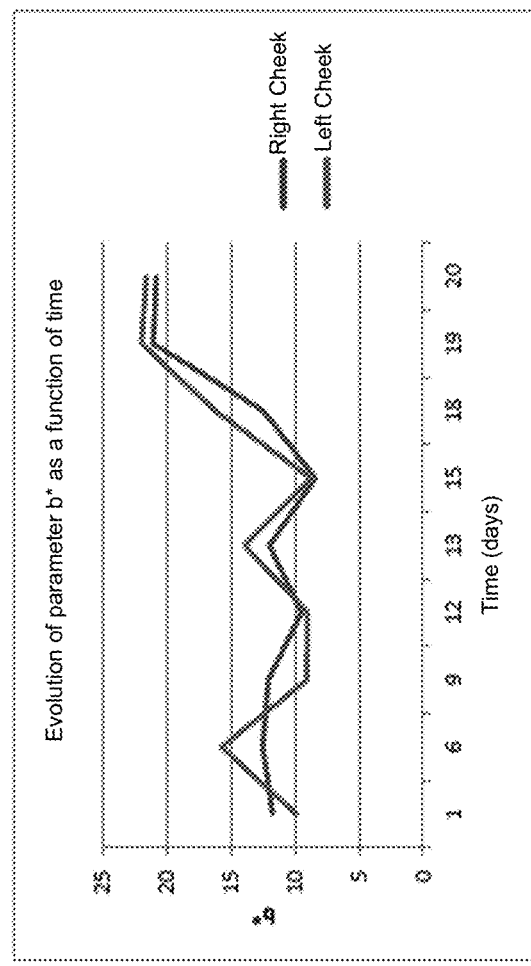

In order to analyze the time effect, the average of the colorimetric data acquired each day is computed. This notably makes it possible to optimize the signal-to-noise ratio. FIGS. 7, 8 and 9 show the trend respectively of the parameters L*, a* and b* as a function of time over 20 days.

Strong deviations are then noted between the right and left cheeks in lightness (L*) notably on the 12th day. That is mainly due to lighting drifts or to shadows cast on the face during the image capture.

The parameter a* (green/red axis) trends in the same way for both cheeks. The parameter b* (blue/yellow) for its part exhibits strong variabilities.

If the general trend of each parameter is studied, a very different trend is observed from the 18th day with a significant reduction of the parameters L* and a* and a significant increase in the parameter b*.

Figure 10:
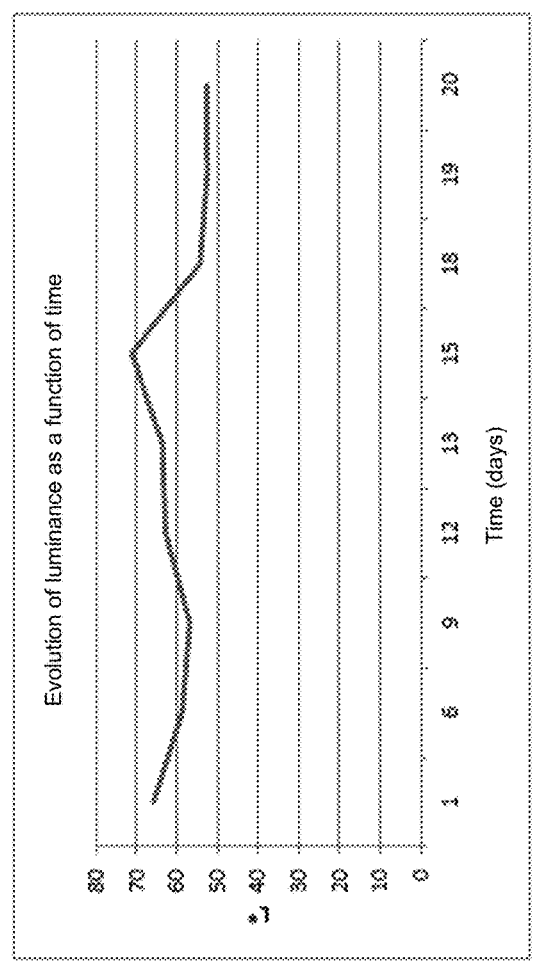
FIGS. 10, 11 and 12 illustrate the trend of each colorimetric parameter for the average of the two cheeks of an individual, per day.
Figure 11:
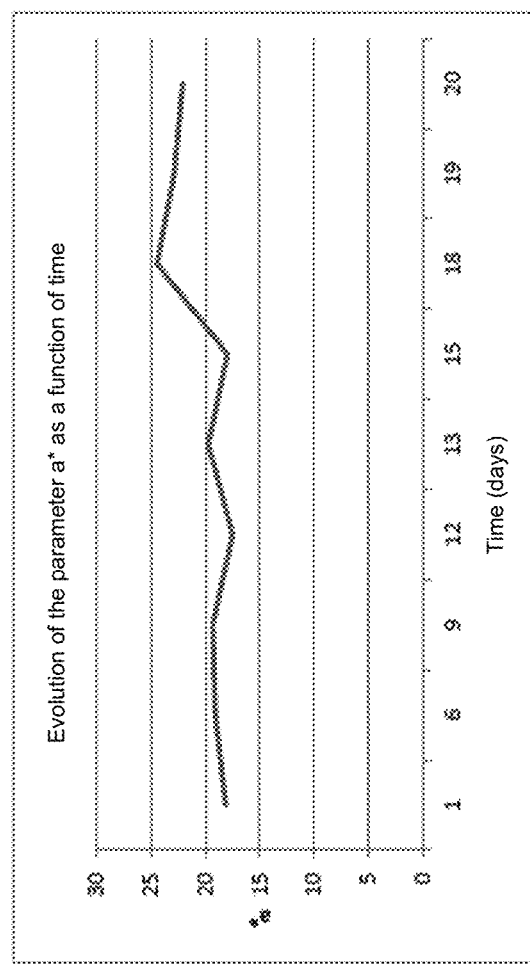
Figure 12:
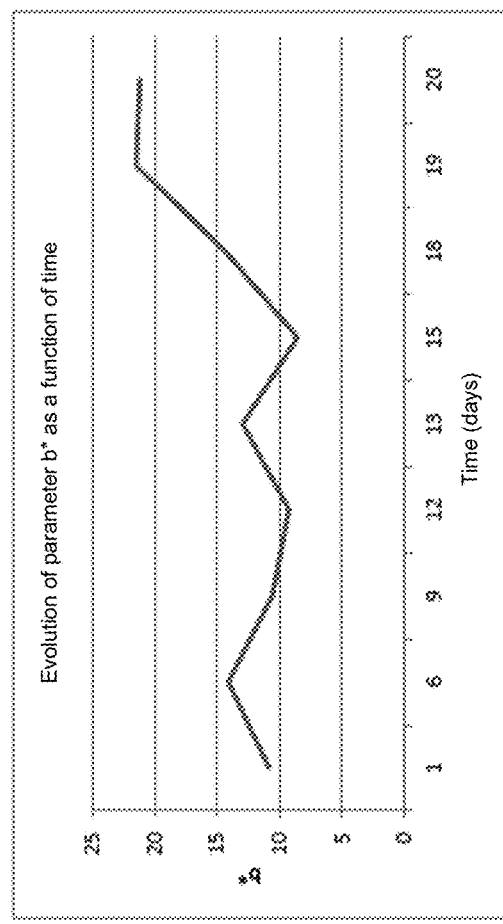

The same trends are found on the graphs of FIGS. 10, 11 and 12, which present the trend of each colorimetric parameter for the average of both cheeks per day.

The time effect will now be analyzed over 17 days.

This analysis was performed on the photos taken by the second individual over 17 days with the first Galaxy S4 device with a total of 84 photos.

The colorimetric data are extracted on both cheeks after colorimetric readjustment with the 30-patch numeric color chart.

The analysis zones were defined manually on each photo as for the preceding analysis.

Figure 13:
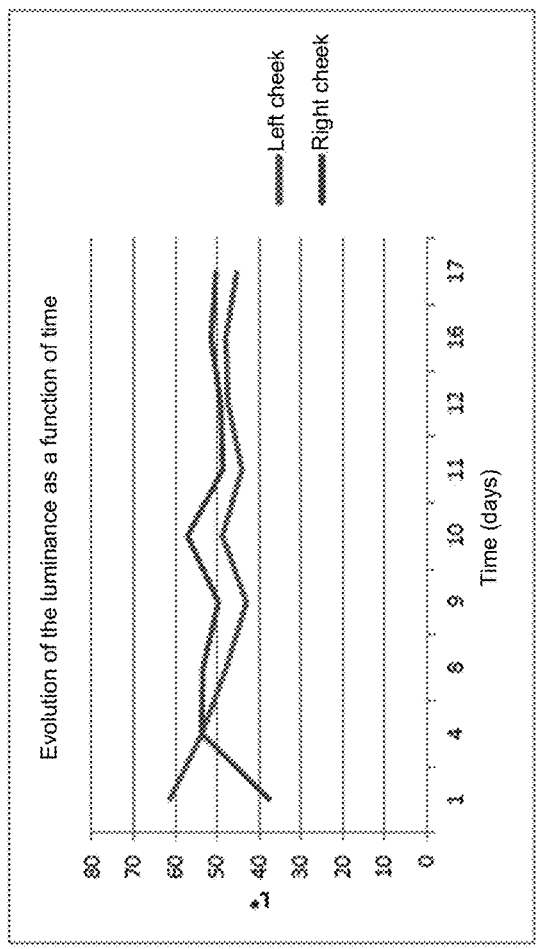
FIGS. 13 to 15 illustrate the trend of all the colorimetric parameters independently for each cheek.
Figure 14:
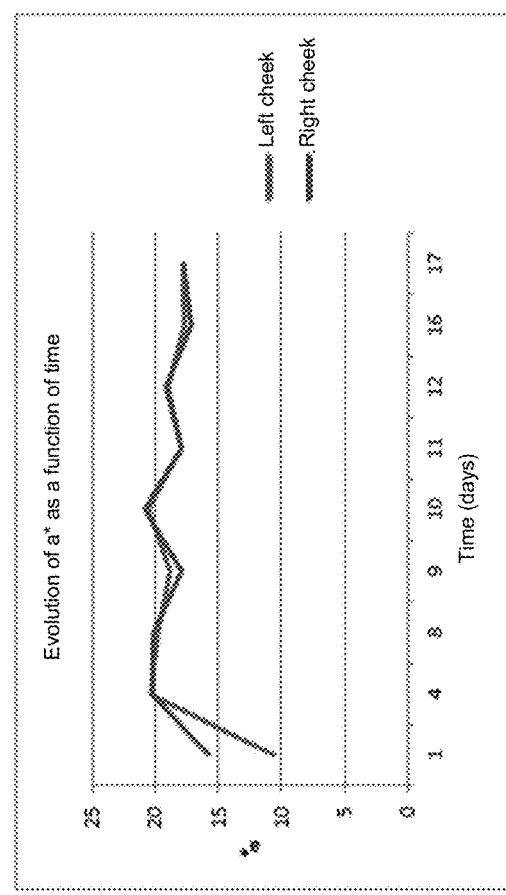
Figure 15:
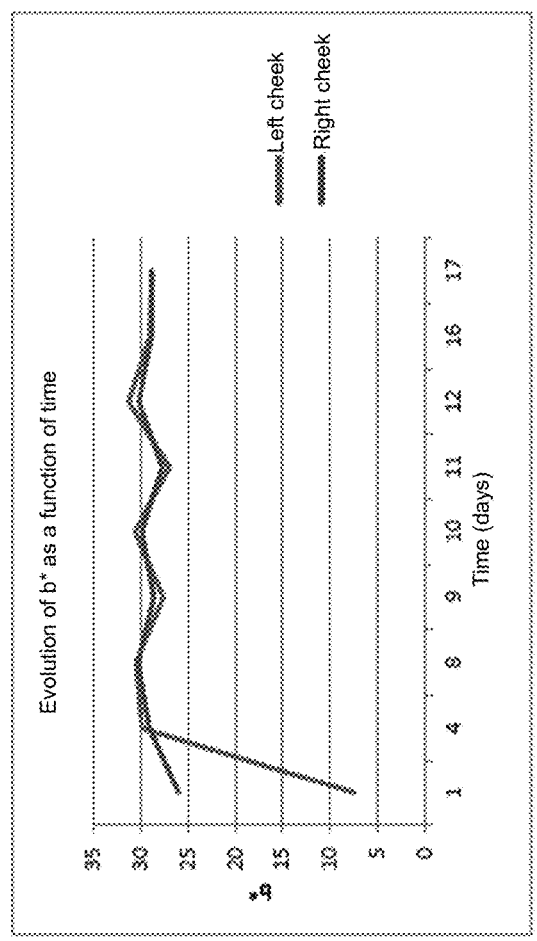

FIGS. 13 to 15 show the trend of all the colorimetric parameters independently for each cheek. The data were averaged for each day.

As illustrated in FIG. 13, it is observed on the first day that the two cheeks are very differently exposed with very different brightness values (20 deviation units). For the other analysis times, the right cheek is always more exposed than the left cheek but in much less significant proportions (5 to 10 deviation units).

The parameter a* (red/green axis), illustrated in FIG. 14, seems identical between the 2 cheeks over time except in the first time.

As for the parameter a*, the parameter b* (yellow/blue axis), illustrated in FIG. 15, is relatively identical whatever the side of the face analyzed except for the first time where the left/right differences are very significant.

Figure 16:
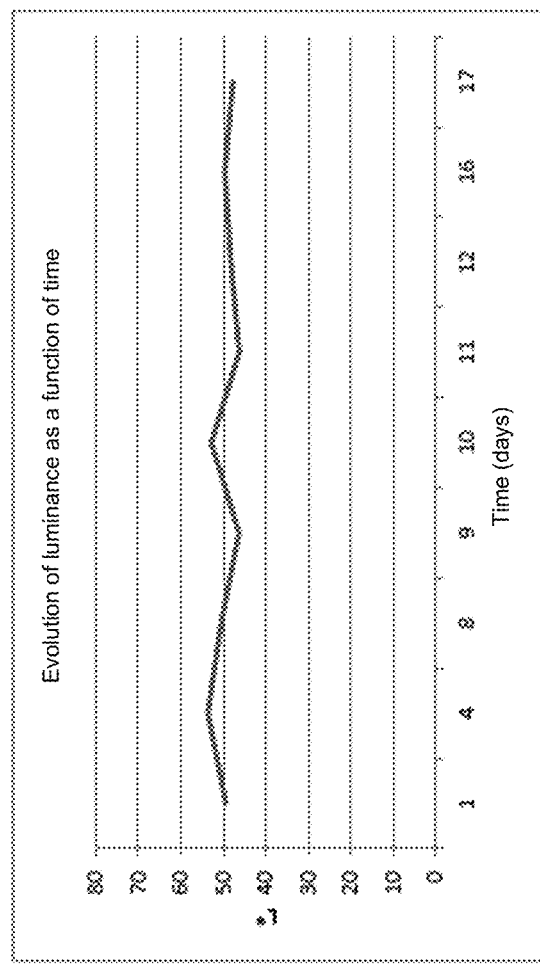
FIGS. 16 to 18 illustrate the overall colorimetric trend of the face (right cheek and left cheek merged together)
Figure 17:
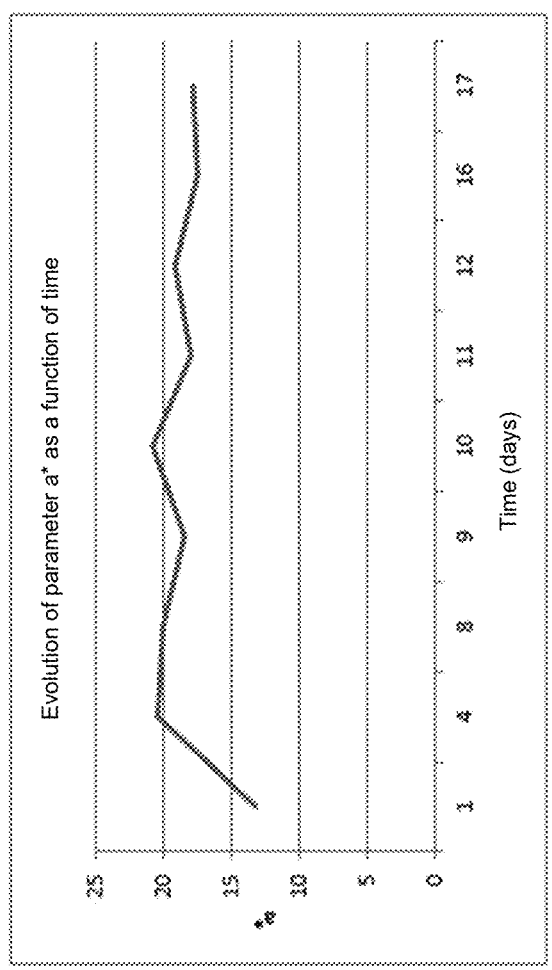
Figure 18:
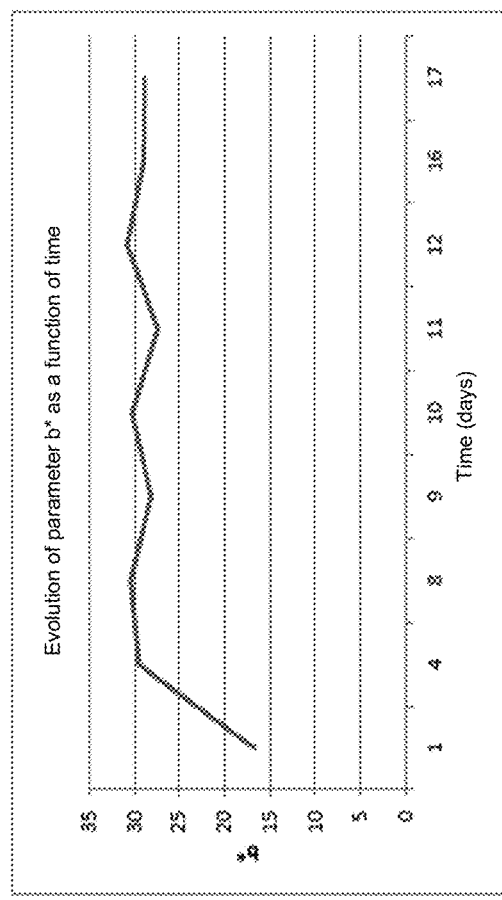
Figure 19B:
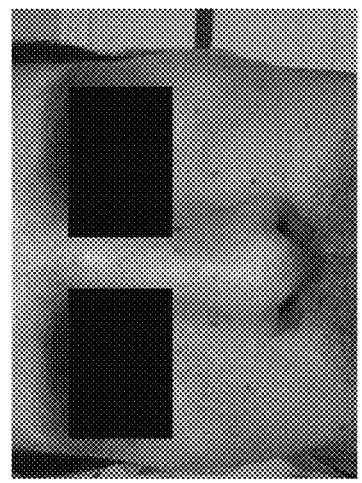
FIGS. 19a, 19b, 20a and 20b illustrate the trend of the color of the skin under the effect of tanning.
Figure 19A:
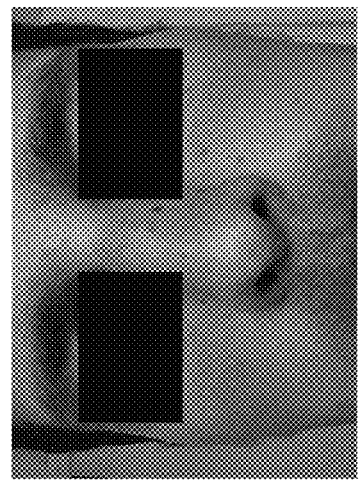
Figure 20B:
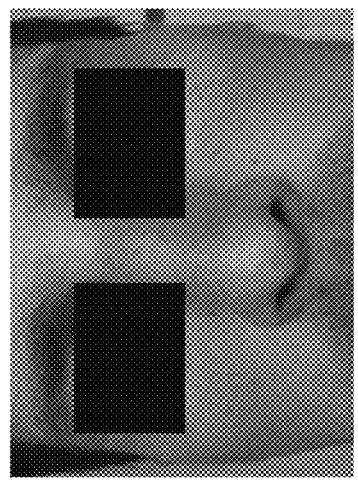
Figure 20A:
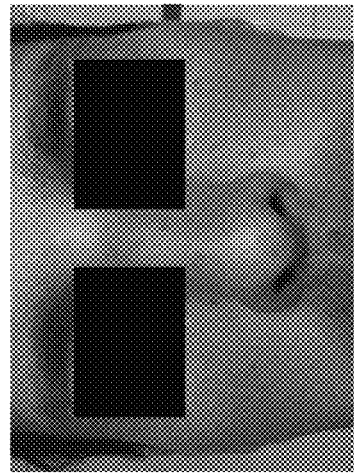

The overall colorimetric trend of the face (right cheek and left cheek merged together) will now be studied, as illustrated in FIGS. 16 to 18.

If only the first time period corresponding to an acquisition problem (linked to a non-uniform lighting on the two cheeks) is considered, a quasi-stability is observed in the different colorimetric parameters L*, a* and b* over time with differences of only a few units.

These results show that the skin of the second individual has not changed colorimetrically during the 17 days of analysis.

The tanning effect on the measurements will now be analyzed.

This analysis was carried out on the photos taken by the second individual over 14 days with the first Galaxy S4 device with a total of 150 photos.

The colorimetric data are extracted on the two cheeks after colorimetric readjustment with the 30-patch numeric color chart.

The analysis zones were defined manually on each photo.

The trend of the color of the skin can be seen in the photos acquired as shown by FIGS. 19a, 19b, 20a and 20b.

Firstly, the colorimetric trend on the two cheeks in the same light environment will be addressed. The photos were acquired in front of a fluorescent tube luminaire in a closed room at the same time every day for 12 days.

The orientation of the face relative to the luminaire was not controlled in order to study the measurement variabilities as a function of the position of the face relative to the illumination.

Three photos were acquired each day and the following graphs show the results obtained over 12 days of analysis.

Figure 21:
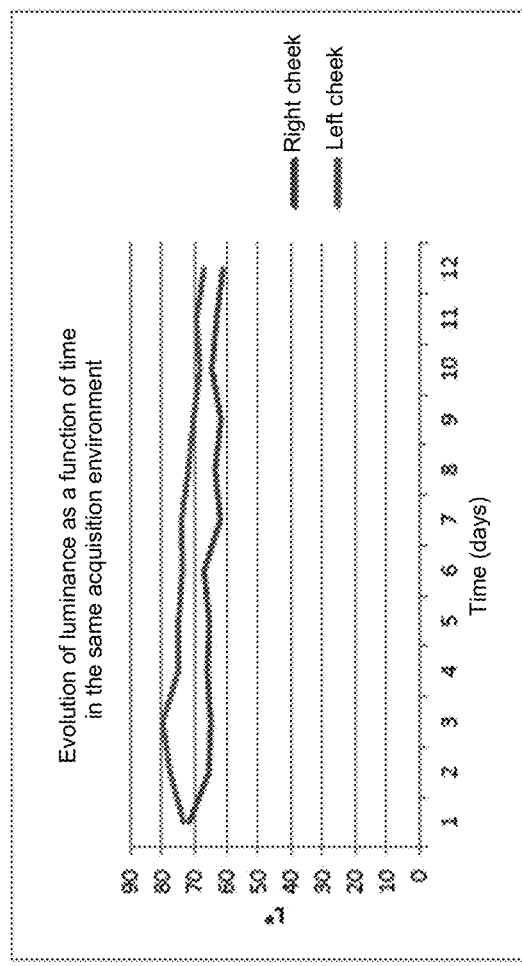
FIGS. 21, 22 and 23 illustrate the colorimetric trend of each cheek.
Figure 22:
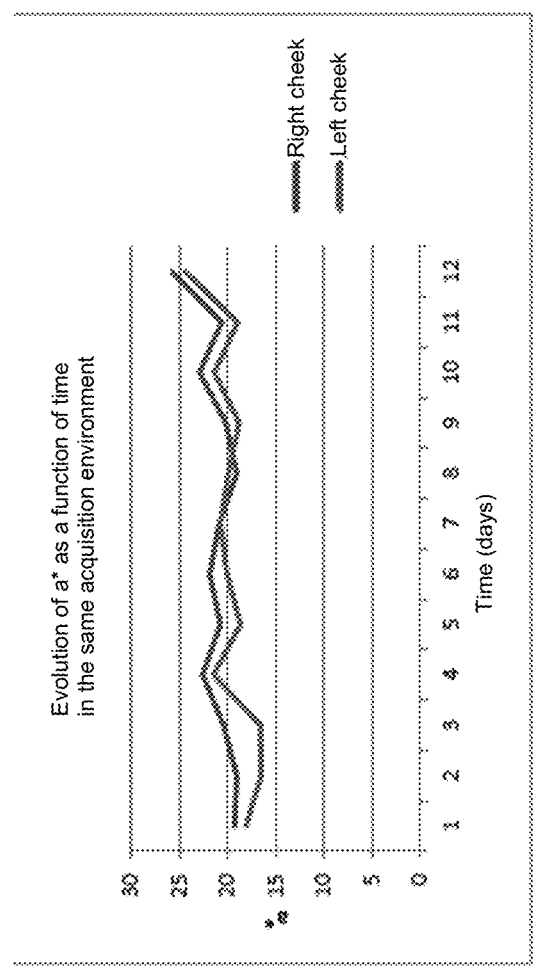
Figure 23:
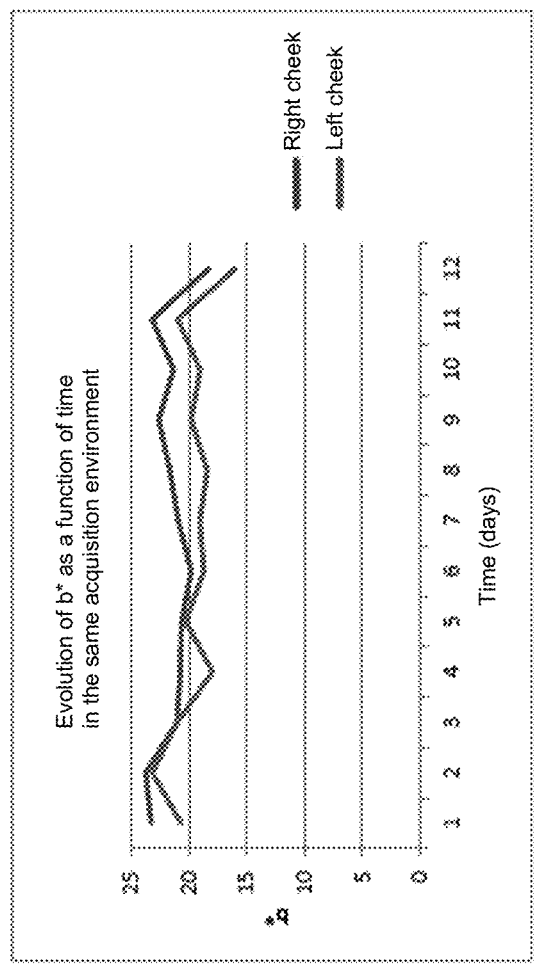

Through FIGS. 21, 22 and 23, it is observed that the left cheek is overall always more overexposed than the right cheek but the trends are similar for all 3 parameters.

The overall trend of the skin on the 2 cheeks at the same time and for all the lighting conditions and all the image captures acquired per day will now be examined. Each day, the average of all the data relating to the photos acquired in the morning, at midday and in the evening in different light environments is calculated. The following graphs then show the trend of the colorimetric parameters L*, a* and b* for each day.

Figure 24:
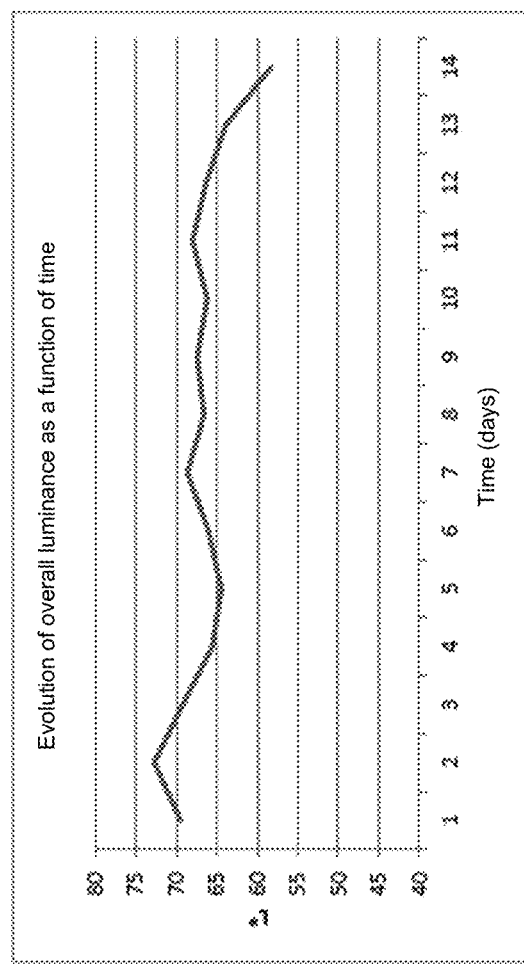
FIGS. 24, 25 and 26 illustrate the overall colorimetric trend.
Figure 25:
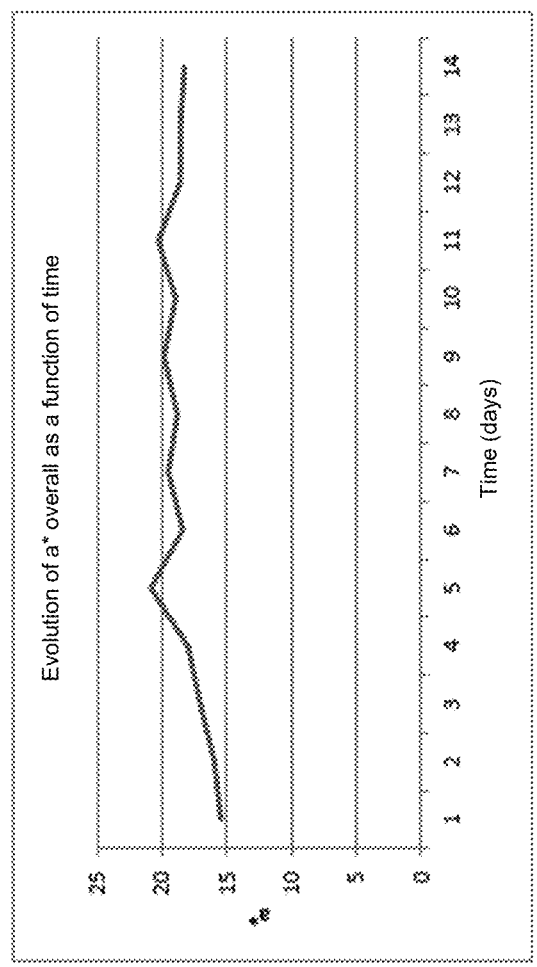
Figure 26:
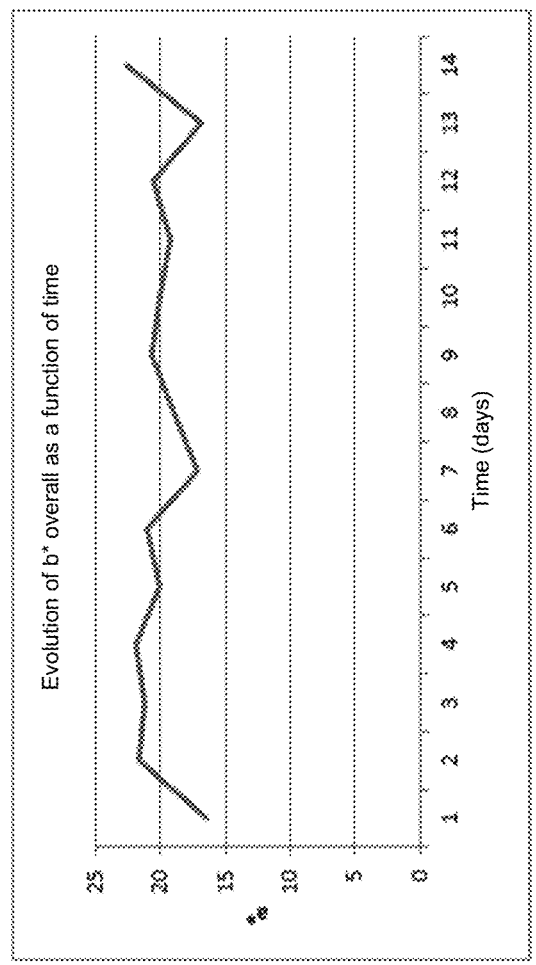

In FIGS. 24, 25 and 26, it is observed that the lightness parameter L* decreases by more than 10 units in 12 days by averaging all the measurements performed each day, i.e. a minimum of 9 photos per day in 3 different lighting conditions each time. That shows that the skin has darkened and therefore exhibits a tanning trend over time.

The more significant changes between the 2nd and the 3rd day and between the 13th and the 14th day correspond clearly to strong exposures to the sun on those days.

In addition, the redness parameter (a*) increases by more than 4 units over the 12 days of analysis which shows a reddening of the skin. For its part, the parameter b* remains virtually constant throughout the study.

As indicated previously, the "SmartCam" data acquisition software makes it possible to record data relating to the different sensors for each acquisition. The influence of the data from these different sensors on the acquisition of the images and the results obtained previously will now be studied, and first of all the different sensors will be analyzed over a period of 12 days.

Figure 27:
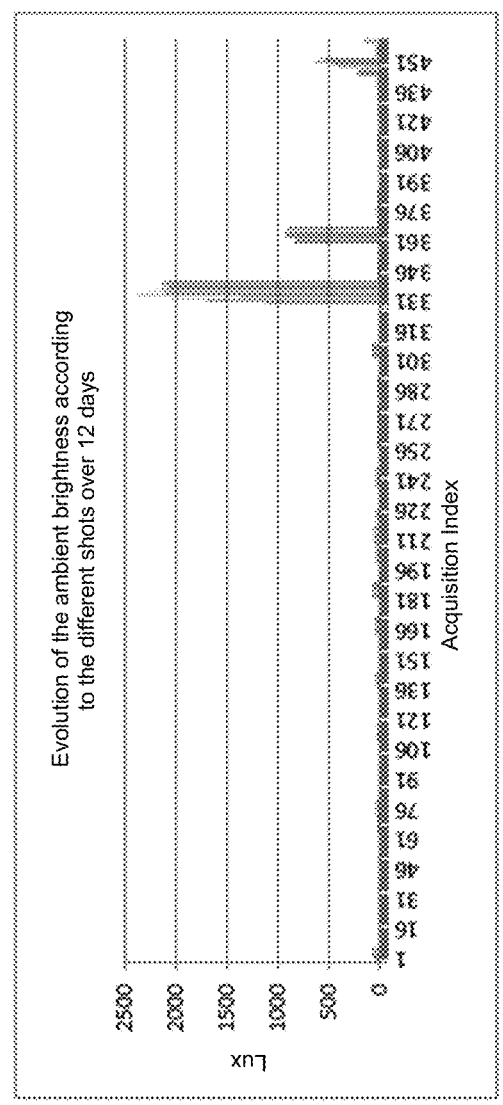
FIG. 27 illustrates the trend of ambient brightness according to different shots over time.

The graph of FIG. 27 presents the data acquired by the third individual over 12 days with the first device, the Samsung Galaxy S4 telephone.

Figure 28B:
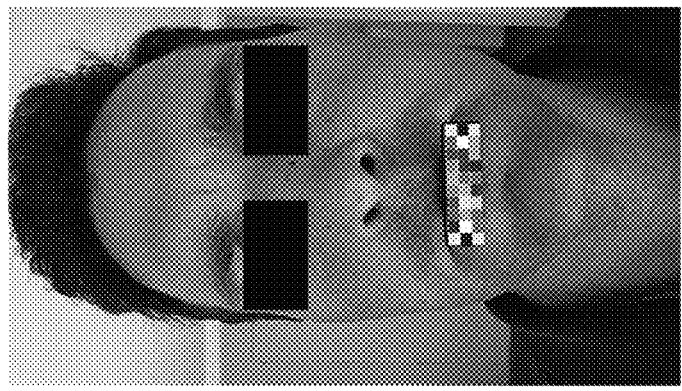
FIGS. 28a and 28b illustrate photos taken with a very high ambient brightness level.
Figure 28A:
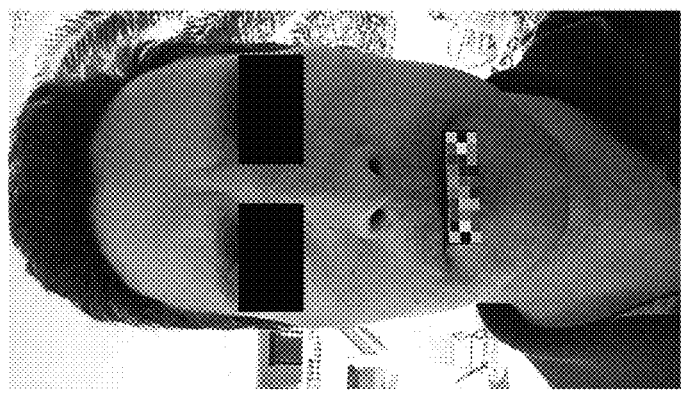

FIGS. 28a and 28b show photos with a very significant ambient brightness level, respectively 2094 lux and 912 lux.

The other data will now be studied as a function of time.

Figure 29:
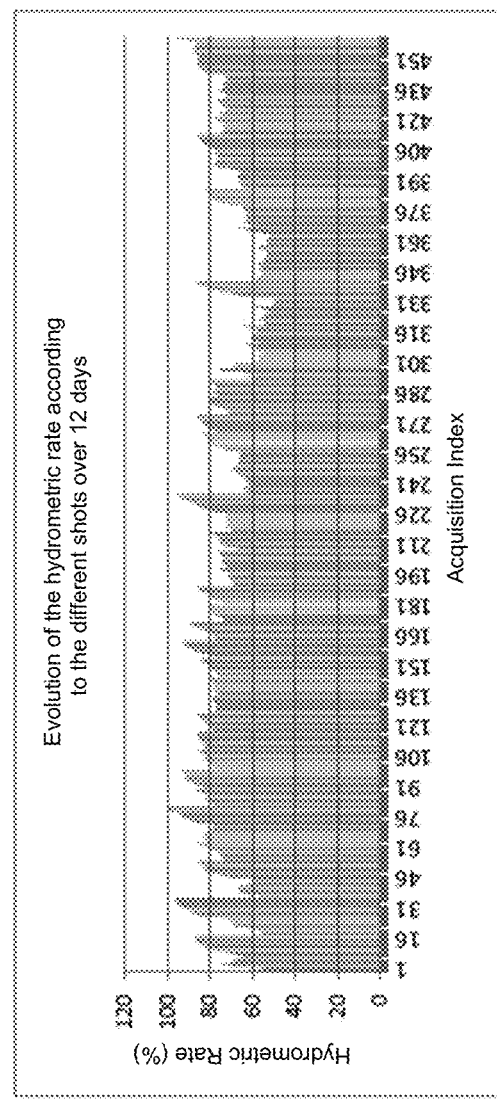
FIG. 29 illustrates the trend of the rate of relative humidity over time.

FIG. 29 illustrates the trend of relative humidity over time. The relative humidity is highly variable as a function of the image capture location. In rooms with water (bathroom for example) the humidity can be very high. No correlation between the ambient humidity and the gloss (L*) on the photos acquired was identified.

Figure 30:
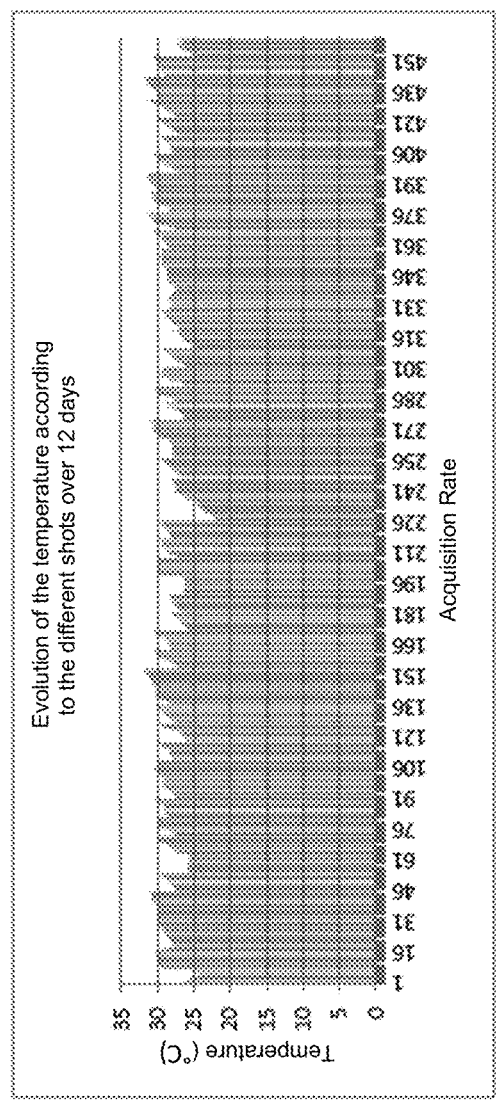
FIG. 30 illustrates the trend of temperature over time.

FIG. 30 illustrates the trend of the temperature over time. The ambient temperature can be an important factor for the sensation of the heat effect during the flush effect. This datum could be used in addition to the heat felt. However, in the context of the feasibility study, no correlation between the temperature and the trend of the colorimetric parameters was observed, the temperature having remained relatively stable during the study (between 23° and 32° C.).

Figure 31:
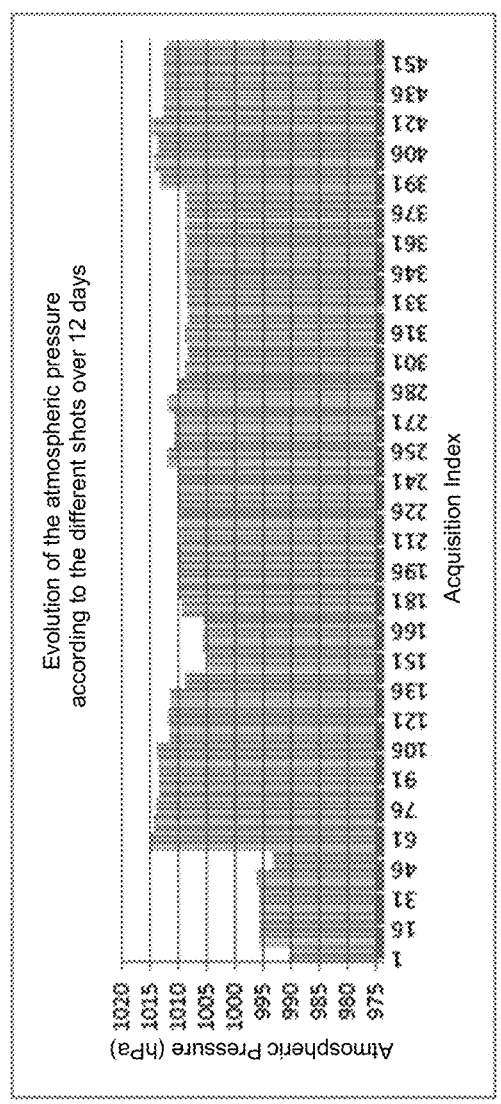
FIG. 31 illustrates the trend of atmospheric pressure over time.

FIG. 31 illustrates the trend of the atmospheric pressure over time. The atmospheric pressure notably shows a change of location at the start of the study but does not allow for a correlation with the measured colorimetric values.

The various sensors will now be analyzed over a period of 15 days.

The data were acquired by the second individual over 15 days with the first device, a Samsung Galaxy S4.

Figure 32:
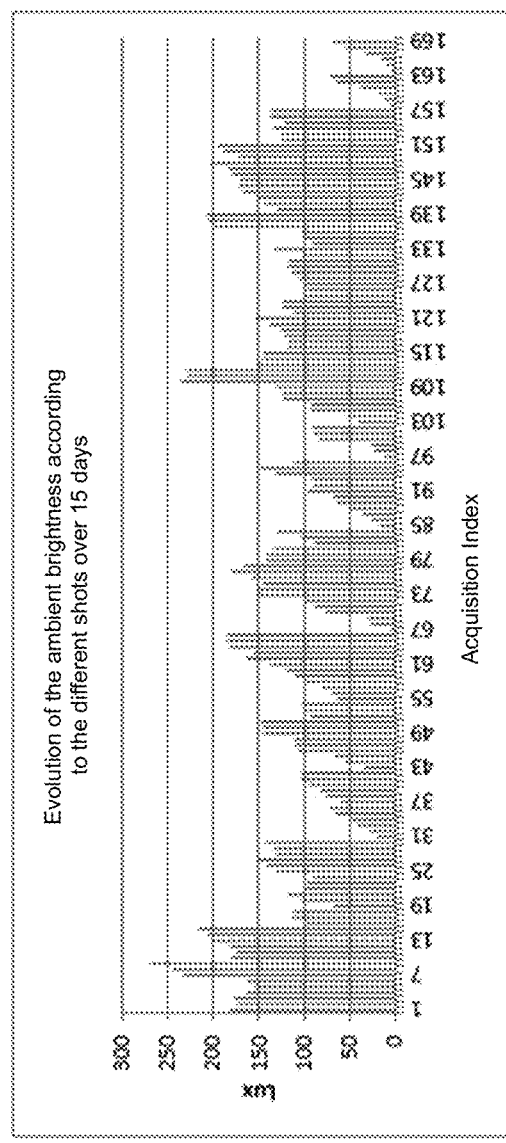
FIG. 32 illustrates the differences in ambient brightness observed on the acquisitions of another person.

The ambient brightness differences observed on the photo acquisitions, illustrated in FIG. 32, are not a source of drift during the acquisition. The variations of 260 lux maximum remain very low.

Figure 33:
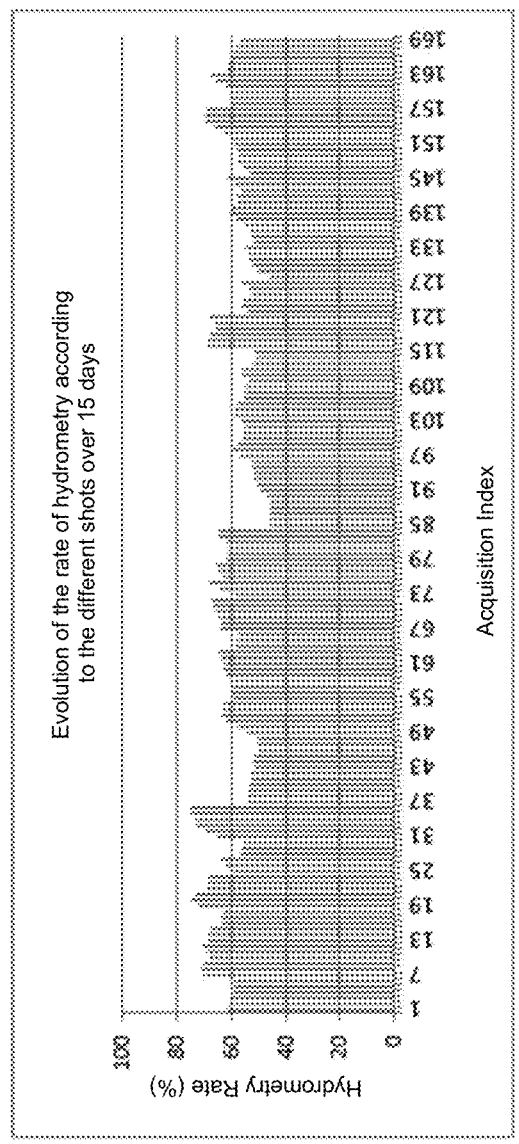
FIG. 33 illustrates the rate of relative humidity as a function of time on the acquisitions of another person.

The relative humidity, illustrated in FIG. 33, varies as a function of time with an overall average of 54%. No correlation between these values and the trend of the colorimetric parameters was identified.

Figure 34:
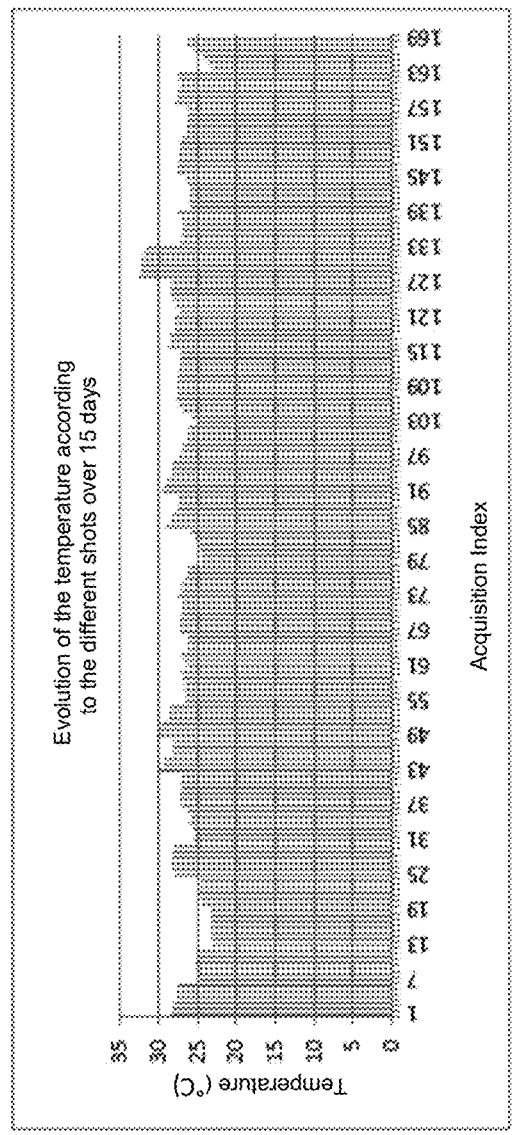
FIG. 34 illustrates the temperature as a function of time on the acquisitions of another person.

The temperature, illustrated in FIG. 34, is also relatively stable and could present an interesting datum for the clinical study. In this study, it has no significant influence on the color of the skin of the cheeks.

Figure 35:
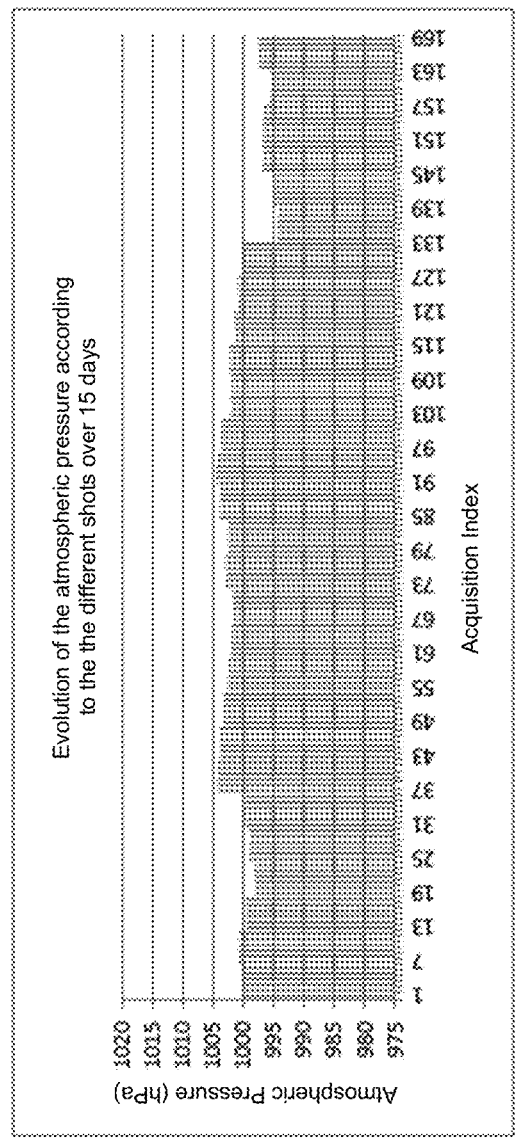
FIG. 35 illustrates the trend of the atmospheric pressure over time on the acquisitions of another person.

There again, the atmospheric pressure, illustrated in FIG. 35, varies slightly but is not an indicator which can be correlated with the color of the skin.

The data were required by the first individual over 20 days with the second device, a Samsung® Galaxy S4 Mini®. This device has only a gyroscope and a brightness sensor.

Figure 36:
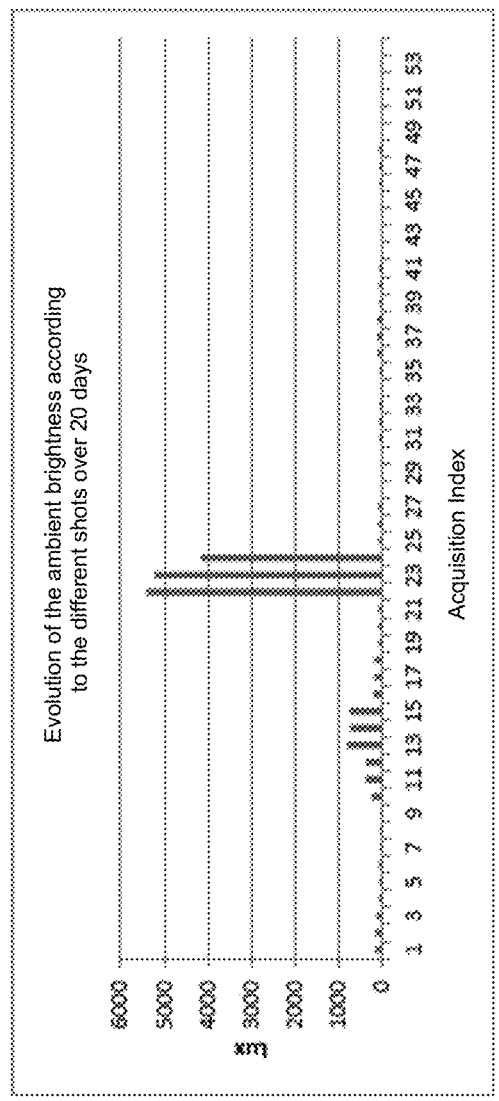
FIG. 36 illustrates the trend of ambient brightness.

The interest here is focused only on the data relating to the ambient brightness as the graph of FIG. 36 shows.

Figure 37:
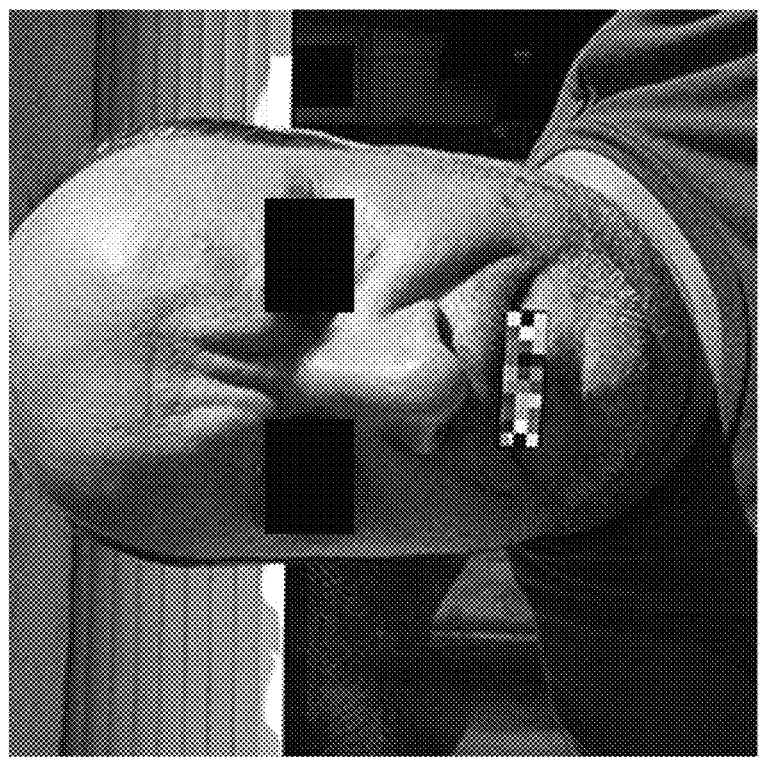
FIG. 37 illustrates photos acquired with an ambient brightness exceeding 4000 lux.

It will then be noted that some photos were acquired with an ambient brightness exceeding 4000 lux. The following FIG. 37 shows a photo relative to these acquisitions.

The tilt of the device will now be studied.

During each acquisition, the information concerning the tilt of the device is stored in the database associated with the "SmartCam" acquisition software.

After analysis of all the device tilt data on each acquisition, given in table 5 below, it is observed that the median value is relatively constant between the subjects. However, the angles of acquisition can vary relatively significantly with a maximum deviation of 30°.

TABLE 5

Image capture tilt angles.

|  | Min | Median | Max |
|---|---|---|---|
| Individual 1 | 73.36° | 85.05° | 105.88° |
| Individual 2 | 73.43° | 87.38° | 100.57° |
| Individual 3 | 66.04° | 84.78° | 96.80° |

Figure 38B:
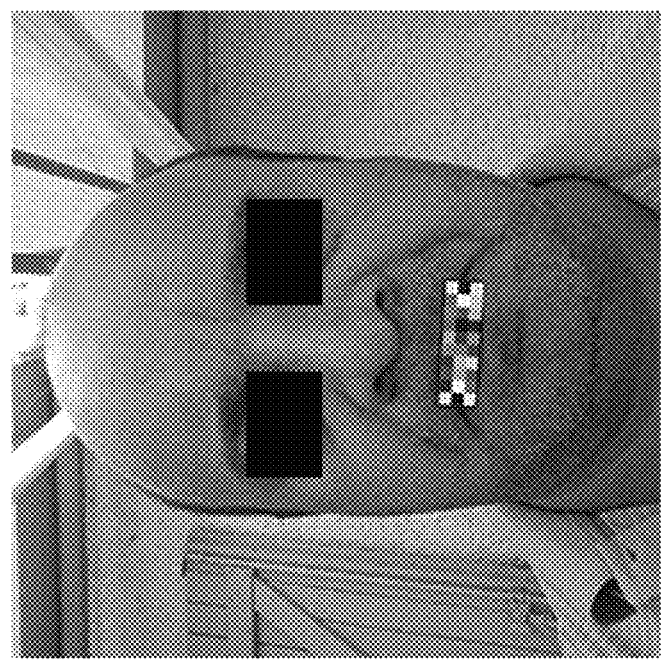
FIGS. 38a, 38b, 39a and 39b illustrate the influence of the vertical inclination on the acquisition of a photograph.
Figure 38A:
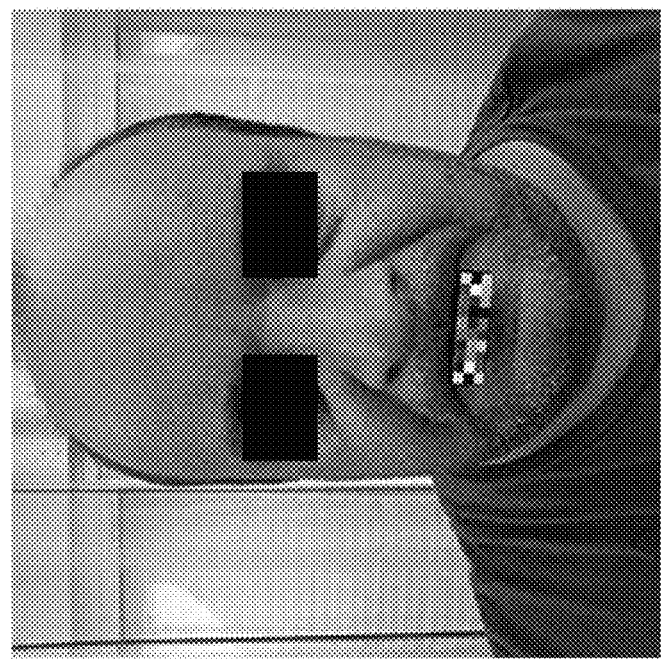
Figure 39B:
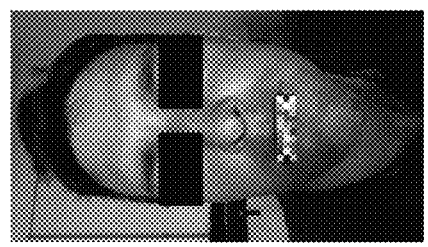
Figure 39A:
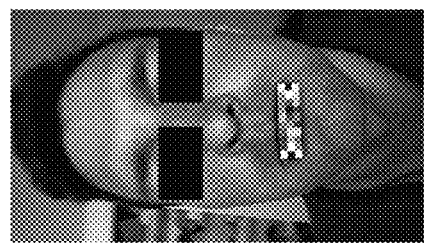

These variations of the tilt angle can modify the analysis zone on the cheeks but also the lighting geometry relative to the image capture axis as FIGS. 38a, 38b, 39a and 39b show. The photograph of FIG. 38a is captured with a vertical tilt of the device at 73° whereas that of FIG. 38b is acquired with a vertical tilt of 105°. The photograph of FIG. 39a is taken with a vertical tilt of the device at 66° whereas that of FIG. 39b is acquired with a vertical tilt of 96°.

In order to best control the orientation of the image capture, it will be necessary to activate the tilt indicator (FIG. 2c) via the administration part of the software making it possible to limit the acquisition angle, between 85° and 95° for example, at the time of the image capture to limit the variabilities linked to the acquisition angle.

In light of the above, the two typical acquisition systems provide images of good quality for an overall colorimetric analysis. The resolution of the images is satisfactory with a rectangular field for the S4 and a square field for the S4 Mini which therefore limits the resolution if the complete face is to be contained within the field.

The first device, which also has a larger screen for real time viewing at the time of acquisition, will therefore be preferred.

A relatively significant JPEG compression effect will however be noted on the resulting photos in large enlargements. These systems do not give access to the raw data (RAW format) of the photos at the sensor output and impose the JPEG format with low compression.

With regard to the software application, the latter is relatively intuitive and offers all the desired functionalities.

Advantageously, a check on the ambient brightness via a brightness sensor incorporated in the smartphone to avoid the overexposure of a particular zone on the face or lighting conditions too far away from the initial conditions is implemented. A message will appear on the screen to warn users if the brightness condition is not satisfactory.

It will however have to evolve to incorporate other functionalities relating to the clinical study.

A number of optimizations are already envisaged:
addition of an ambient brightness check to avoid the overexposure of a particular zone on the face or lighting conditions too far away from the initial conditions,
addition of a check of the acquired image to validate the sharpness and thus limit blur from movement,
addition of a validation of the colorimetric consistency between different zones of the face (2 cheeks and forehead) to try to best limit the lighting drifts,
addition of one or more colorimetric reference zones on the face at T0 to try to limit the drifts from one acquisition to another, and
provision of a white screen with a maximum brightness during image capture to try to obtain a relatively significant lighting originating from the device.

Moreover, the 3 color charts are suitable for the step of colorimetric readjustment of the images. However, the numeric color chart seems most appropriate because it makes it possible to adjust not only the color temperature, as with the gray color chart, but also to optimize certain specific hues.

The Munsell color chart, although very diffuse, is no more efficient than the color chart produced by digital printing given the great lighting variations.

The color chart support produced for this study seems suitable for a good repositioning in front of the subject. Its dimensions will be able to be optimized if necessary.

The main problem for the colorimetric readjustment is that the colorimetric variations on the color chart do not take account of all the variations on the face because of the excessive differences of lighting geometry. That is why it is necessary to try to best constrain the light environment during image capture. A very diffuse uniform lighting would be ideal.

The colorimetric data will now be analyzed.

The colorimetric color chart makes it possible to optimize by almost 50% the colorimetric drifts between each image capture.

After readjustment of the images, the repeatability of the system is of the order of 1.5 units in L* and approximately 1 unit in a* and b* in uniform lighting conditions.

In non-uniform lighting conditions on the zone of the face, the variation of geometry from one image capture to another can lead to deviations of 7 units in L* and b* and of 4 units in a* at most. These variations are all the greater if the location and type of lighting are changed.

However, it is possible, by averaging all the data, to obtain interesting results on the colorimetric trend of the skin such as the effect of tanning over time.

In the context of the analysis of the flush effect, it will therefore be necessary to multiply the acquisitions to optimize the signal/noise ratio.

A number of solutions need to be explored:
using the magnetometer to require the user to change orientation and therefore change the lighting geometry,
using specific colorimetric parameters like the dH (chromatic tonality deviation) which does not take account of the lightness L*,
using parameters that are unchanging as a function of the shadows such as the normalized RGB space or specific spaces of L1L2L3 type,
using the parameter a* which seems less influenced by the light environment and which takes account of the rednesses, and
using reference zones on the skin like the chin or the forehead to perform a calculation of contrast between the "healthy" skin and the skin "with flush effect".

Furthermore, the colorimetric data can be analyzed advantageously for a self-assessment of the skin disorders such as melasma, nevus, rosacea, erythema, reddening, acne, psoriasis, dermatitis, actinic keratosis, rash and seborrheic dermatitis.

It is moreover possible to use various types of sensors provided in the image capture devices.

The temperature, pressure and relative humidity sensors present in the first telephone make it possible to extract information that is of interest but does not necessarily help in stabilizing the image capture or in controlling the acquisition environment.

By contrast, the brightness and tilt (gyroscope) sensors, which are also present in the second device, can help to constrain the image capture.

Thus, the various sensors of the image capture devices are used to acquire parameters notably even so to image capture conditions. The "SmartCam" acquisition software application is then programmed to correct the colorimetric components of the effect of the parameters measured on the face.

In other words, it will be possible to incorporate a real time preview of these sensors at the image capture time to constrain the user to correctly position his or her device or to change the location because the light ambience is much too great (greater than 500 lux for example).

In order to optimize the image capture in very high resolution, other lenses, such as those marketed under the Sony® brand can be used. These lenses connected to a smartphone connect by Wi-Fi to an Android smartphone or to an iPhone® and make it possible to perform image captures of excellent quality. Currently, the JPG format is the only one supported, the RAW format will come later.

The QX10 lens consists of an 18.2 megapixel Exmor R CMOS sensor to which is added a Carl Zeiss®×3.6 zoom. An optic offering an aperture of between 3.5 and 3.9 with a microphone and a button dedicated to the shutter. The QX100 consists of a 20.2 megapixel CMOS sensor, a 3.6× f/1.8 optical zoom, a microphone, a button dedicated to the shutter and two rings for the manual settings.

The lenses are adapted to the smartphone and a specific Sony® application makes it possible to take snapshots. The smartphone is therefore used to drive the photo lens. It will be necessary to know if it is possible to drive these lenses with an external application. Their price lies between 250 and 450 US Dollars.

The various functionalities of these Sony lenses include various fixing modes, Wi-Fi and NFC connections, Android and iOS compatibility, the direct display of the images on the screen of the connected terminal, simultaneous backup on the lens and the connected smartphone, manual controls from the smartphone which makes it possible to drive the lenses directly from the connected terminal, video recording in 1080p full HD.

Figure 40B:
FIGS. 40a and 40b illustrate two deported and connected lenses.
Figure 40A:

The Sony QX10, illustrated in FIG. 40a, is constructed around a 1/2.3" Exmor CMOS photo sensor with a definition of 18 million pixels. Its stabilized 10× zoom covers the 25-250 mm focal range with apertures of f/3.3-5.9. For the image processing, it benefits from the BIONZ processor. The sensitivity extends from 100 to 12 800 ISO according to the image capture modes. Its dimensions are 6.24×6.18×3.33 cm for a weight of 90 grams.

The Sony® QX100, illustrated in FIG. 40b, is constructed around a 1" Exmor CMOS photo sensor with a definition of 20 million pixels and an x 3.6 stabilized (Carl Zeiss®) optic covering the 28-100 mm focal range. Its apertures are f/1.8-4.9. The QX100 benefits also from the BIONZ image processing processor. Its sensitivity extends from 160 to 25 600 ISO. Its dimensions are 6.25×6.25×5.55 cm for 179 grams.

A practical use of the software application embedded in the image capture systems will now be described with reference to FIGS. 41a, 41b, 42a, 42b and 43, in the context of a treatment of a flush with the medicine Brimonidine.

In order to test the software application embedded in the telephones, a clinical trial relating to a flush treatment with Brimonidine was carried out, during which image captures were done using the "SmartCam" acquisition software.

This study in phase IIa, generally designed to assess dosage needs, comprises two periods. To take account of the variations between individuals, this study was designed to improve the statistical power in the first period and a study plan was provided in the second period. Advantageously, it is a double blind randomized study with random distribution and controlled placebo.

The first period is carried out in a treatment center and comprises three sessions. It lasts one week.

The second period lasts four weeks and is carried out by a subject at home. It is used to validate the reddening model and identify problems or difficulties.

24 subjects with ETR (Erythematotelangiectatic rosacea) and 12 subjects with PPR (Papulopustular rosacea) participated in this study.

The complete study lasts approximately 13 weeks. There is a subjective participation of 5 weeks and a screening period of up to 4 weeks for each subject.

The first period of the study based on the flush model (reddening) is performed in a treatment center. This period aims to produce an objective assessment of the intra-individual variability on each subject.

In this first week of the study, tests are put in place on half-faces of each subject with two different treatments: Excipient (equivalent to placebo, non-active) and Brimonidine 0.5% (product to be tested, active).

Figure 41A:
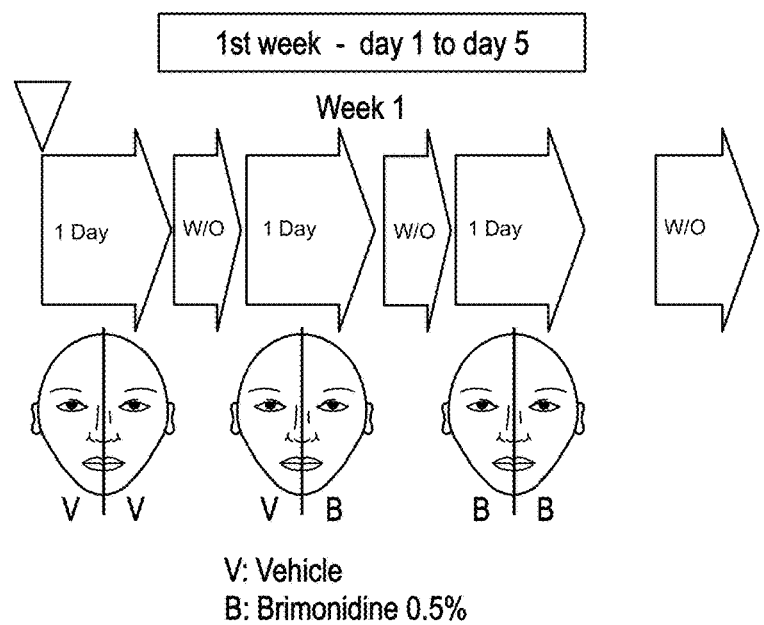
FIGS. 41a and 41b illustrate two phases of data acquisition for testing a data acquisition software application.

As illustrated in FIG. 41a, the excipient is applied to the two half-faces of the subject in the first day. Two days later, the one treatment based on Brimonidine 0.5% is applied to one of the two half-faces of the subject. In the fifth day, all the excipients are replaced by Brimonidine 0.5%.

Figure 41B:
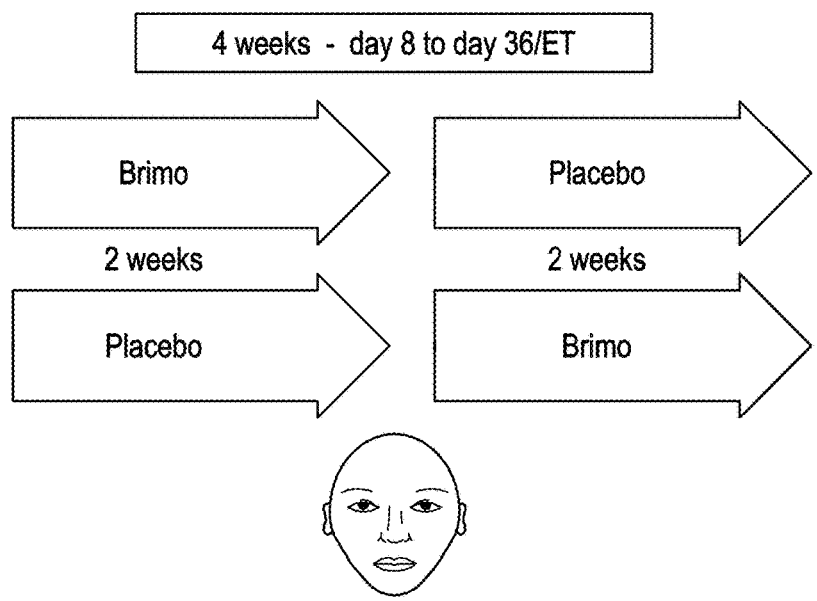

The second period of the study is carried out in the home by each subject via a smartphone. It is a subjective assessment based on trials in two parallel groups (FIG. 41b).

The second period lasts 4 weeks. A first group of subjects applies a treatment based on Brimonidine to the full face and the placebo is applied for a second group of subjects during the first two weeks. In the next two weeks, the two groups of subjects swap their remaining products.

During the second period of the study, each subject uses the first smartphone and the "SmartCam" data acquisition software.

As indicated previously, the software application allows for the rapid repositioning of the subject using the two horizontal axes and a vertical axis and control of vertical alignment of image acquisition using the gyroscope sensor of the smartphone.

The acquisition methods are identical to those described above. The numeric color chart is adopted in this period of the study. Each subject must take a first reference photo in the morning (on rising) and an additional photo on each flush effect during the day.

Figure 42A:
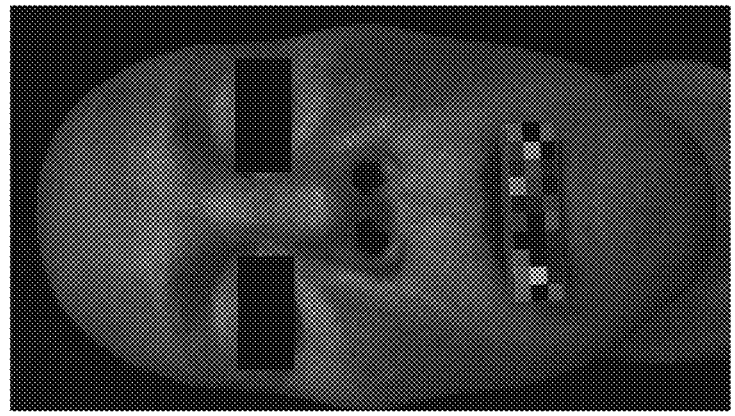
FIGS. 42a and 42b are two photos of a subject taken during the phases of FIGS. 41a and 41b, respectively in the morning and upon a flush effect.
Figure 42B:
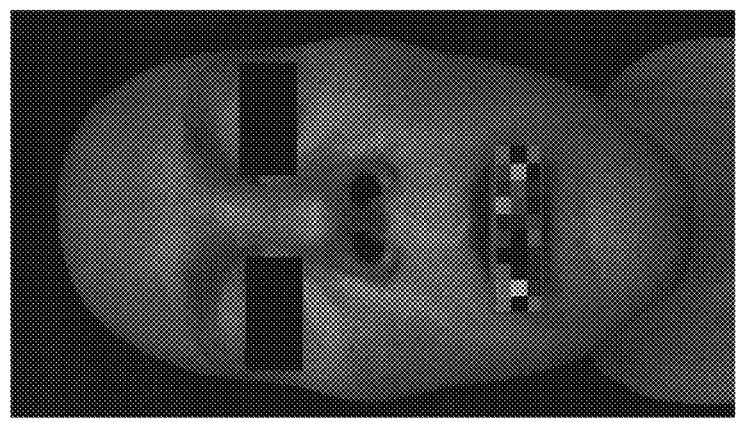

FIGS. 42a and 42b show an example of a subject in the eleventh day of the second period. The photo that can be seen in FIG. 42a is taken in the morning at 08:20 and considered to be the reference. Upon a flush effect at 15:59, an additional photo is taken (FIG. 42b). The cheeks (left and right) of the subject in FIG. 42b are notably much redder than those shown in the morning photo (FIG. 42a).

The results of the study in the second period on the change of the colorimetric parameter a* since the morning are shown in table 6. The abbreviations PP and ITT in table 6 correspond respectively to the "per protocol" and "intention-to-treat" analyses known to those skilled in the art.

It can be seen that the averages and medians of the average a* change since the morning are always positive. In other words, the cheeks during flush effects are redder than in the morning. The fact that the 95% confidence interval is situated between [0.47, 2.07] confirms the capacity of the software application to detect the flushes.

TABLE 6

Change of a* average since the morning.

| Average a* change since the morning | | Brimonidine 0.5% | Placebo | Total |
|---|---|---|---|---|
| First two weeks/PP | Number | 14 | 16 | 30 |
| | Average ± σ | 1.15 ± 3.24 | 1.34 ± 2.10 | 1.25 ± 2.64 |
| | Median | 0.92 | 1.04 | 0.93 |
| | (min, max) | (−4.3, 10.2) | (−1.4, 5.9) | (−4.3, 10.2) |
| First two weeks/ITT | Number | 15 | 16 | 31 |
| | Average ± σ | 1.44 ± 3.32 | 1.34 ± 2.10 | 1.39 ± 2.71 |
| | Median | 0.94 | 1.04 | 0.94 |
| | (min, max) | (−4.3, 10.2) | (−1.4, 5.9) | (−4.3, 10.2) |
| Last two weeks/PP | Number | 15 | 14 | 29 |
| | Average ± σ | 1.47 ± 2.91 | 1.2 ± 2.51 | 1.34 ± 2.68 |
| | Median | 1.98 | 1.58 | 1.67 |
| | (min, max) | (−4.1, 5.5) | (−2.9, 5.3) | (−4.1, 5.5) |
| Last two weeks/ITT | Number | 15 | 14 | 29 |
| | Average ± σ | 1.47 ± 2.91 | 1.2 ± 2.51 | 1.34 ± 2.68 |
| | Median | 1.98 | 1.58 | 1.67 |
| | (min, max) | (−4.1, 5.5) | (−2.9, 5.3) | (−4.1, 5.5) |
| Total/PP | Number | 29 | 30 | 59 |
| | Average ± σ | 1.32 ± 3.02 | 1.34 ± 2.10 | 1.25 ± 2.64 |
| | Median | 1.49 | 1.26 | 1.31 |
| | (min, max) | (−4.3, 10.2) | (−2.9, 5.9) | (−4.3, 10.2) |
| Total/ITT | Number | 30 | 30 | 60 |
| | Average ± σ | 1.46 ± 3.074 | 1.27 ± 2.26 | 1.37 ± 2.67 |
| | Median | 1.58 | 1.26 | 1.40 |
| | (min, max) | (−4.3, 10.2) | (−2.9, 5.9) | (−4.3, 10.2) |

Moreover, the software application also makes it possible to study the distribution of the flushes during the day by virtue of the time data (date and time) stored, relative to each image capture.

Figure 43:
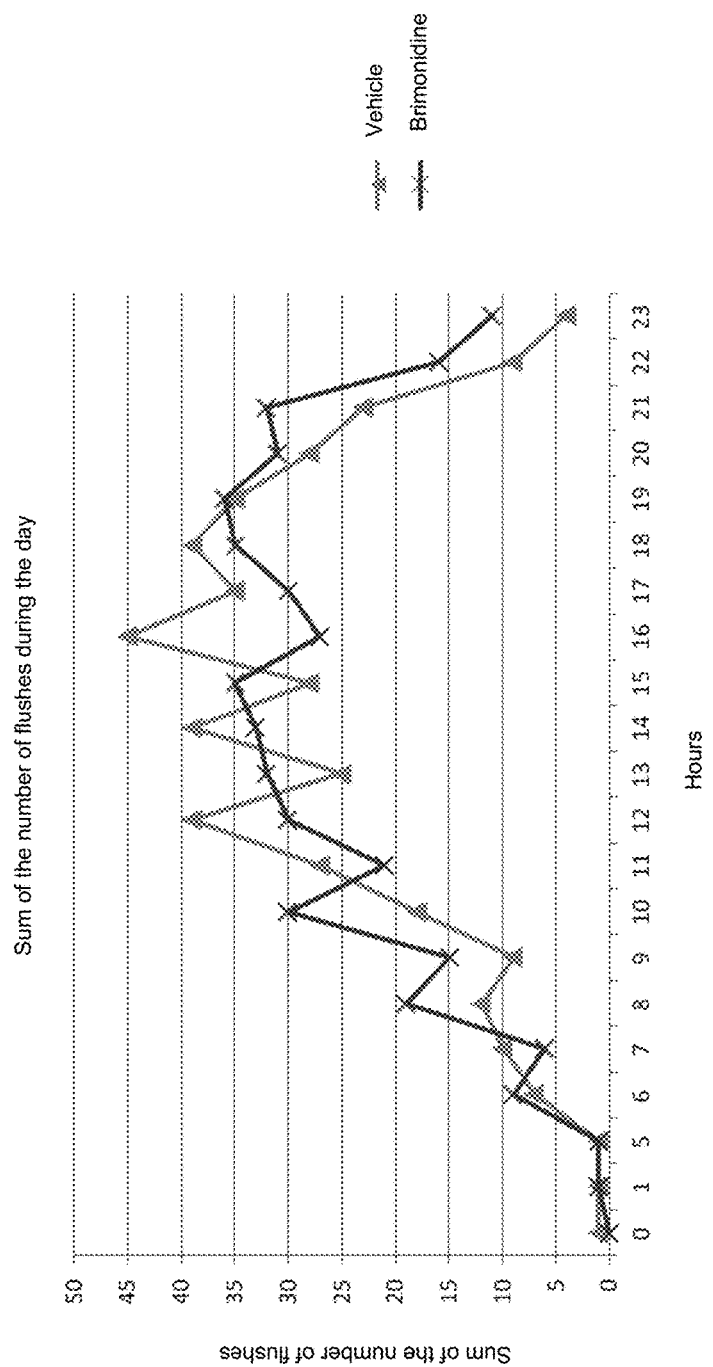
FIG. 43 illustrates the trend of the number of flushes during the day recorded by the acquisition software according to the invention.

As illustrated in FIG. 43, the sum of the number of flushes distributed throughout the day can be observed. There are more flushes in the afternoon (12 h-19 h) than in the rest of the time of the day. The application of a treatment makes it possible to reduce the occurrence of the flushes in this period of the day. These important data can then be analyzed in order to end a treatment.

With the capacity to detect flushes and record their distributions during the day, the application thus makes it possible to perform self-assessments of skin disorders such as melasma, nevus, rosacea, erythema, reddening, acne, psoriasis, dermatitis, actinic keratosis, rash and seborrheic dermatitis.

The invention claimed is:

1. A method of analyzing facial images of a human being, the method comprising the following steps:
   acquiring at least one image of the human being's face, wherein the human being's nose, eyes and cheeks are aligned on pre-existing markers;
   measuring a colorimetric component L* (lightness), a* (red/green), or B* (yellow/blue) of the image in at least one zone of the face;
   comparing the measured colorimetric component to a stored colorimetric value; and
   determining the presence of a flush effect if the measured colorimetric component is greater than the stored colorimetric value.

2. The method as claimed in claim 1, in which the at least one zone of the face is a cheek of the human being's face.

3. The method as claimed claim 1, wherein the stored colorimetric value is a value of the colorimetric component measured at an earlier date for the same face.

4. The method as claimed in claim 1, wherein the presence of a flush effect is determined if a colorimetric component associated with a red face color is greater than a stored colorimetric value associated with the color red.

5. The method as claimed in claim 1, wherein the image acquisition is performed with a smartphone.

6. The method as claimed claim 1, wherein a vertical alignment of the acquisition of the image is ensured via an internal sensor of a smartphone.

7. The method as claimed in claim 1, wherein the acquisition is performed while the human being holds a colorimetric color chart via the mouth, in order to correct the colorimetric components.

8. The method as claimed in claim 1, wherein the colorimetric component of any environmental effect on the human being's face is corrected by acquiring at least one parameter selected from the group consisting of temperature, atmospheric pressure, ambient brightness and relative humidity.

9. The method as claimed in claim 1, wherein the measured value of the colorimetric component is configured for a self-assessment of a skin disorder.

10. The method as claimed in claim 9, wherein the skin disorder is one or more disorders selected from the group consisting of melasma, nevus, rosacea, erythema, reddening, acne, psoriasis, dermatitis, actinic keratosis, rash and seborrheic dermatitis.

* * * * *